(12) United States Patent
Chajut et al.

(10) Patent No.: US 8,822,144 B2
(45) Date of Patent: Sep. 2, 2014

(54) COMPOSITIONS AND METHODS FOR PROGNOSIS AND TREATMENT OF PROSTATE CANCER

(75) Inventors: Ayelet Chajut, Ramat Hasharon (IL); Shai Rosenwald, Nes Ziona (IL)

(73) Assignee: Rosetta Genomics Ltd., Rehovot (IL)

( * ) Notice: Subject to any disclaimer, the term of this patent is extended or adjusted under 35 U.S.C. 154(b) by 0 days.

(21) Appl. No.: 13/390,995

(22) PCT Filed: Jul. 20, 2010

(86) PCT No.: PCT/IL2010/000575
§ 371 (c)(1),
(2), (4) Date: Feb. 24, 2012

(87) PCT Pub. No.: WO2011/021177
PCT Pub. Date: Feb. 24, 2011

(65) Prior Publication Data
US 2012/0232124 A1     Sep. 13, 2012

Related U.S. Application Data

(60) Provisional application No. 61/235,011, filed on Aug. 19, 2009.

(51) Int. Cl.
*C12Q 1/68* (2006.01)

(52) U.S. Cl.
USPC .............. 435/6; 435/325; 435/375; 536/24.5

(58) Field of Classification Search
None
See application file for complete search history.

(56) References Cited

U.S. PATENT DOCUMENTS

| | | | |
|---|---|---|---|
| 6,506,559 B1 | 1/2003 | Fire et al. | |
| 2005/0107325 A1 | 5/2005 | Manoharan et al. | |
| 2005/0182005 A1 | 8/2005 | Tuschl et al. | |
| 2009/0143326 A1* | 6/2009 | Obad et al. | 514/44 |
| 2009/0192114 A1 | 7/2009 | Ovcharenko et al. | |
| 2011/0054009 A1* | 3/2011 | Croce et al. | 514/44 A |

FOREIGN PATENT DOCUMENTS

| | | | |
|---|---|---|---|
| WO | WO 93/23569 A1 | 11/1993 | |
| WO | WO 99/04819 A1 | 2/1999 | |
| WO | WO 99/05094 A1 | 2/1999 | |
| WO | WO 2011/021177 A3 | 2/2011 | |

OTHER PUBLICATIONS

Gandellini et al. (Cancer Research Feb. 24, 2009,: 69: 2287-2295).*
Akhtar et al., Trends Cell Bio., 1992, 2, 139.
Bartel et al., "MicroRNAs: At the Root of Plant Development?" Plant Physiology, Jun. 2003, pp. 709-717, vol. 132.
Bartel, D.P., "MicroRNAs: Genomics, Biogenesis, Mechanism, and Function," Cell, Jan. 2004, pp. 281-297, vol. 116.
Bastide et al., "A Nod Scid mouse model to study human prostate cancer," Prostate Cancer and Prostatic Diseases, 2002, pp. 311-315, vol. 5.
Brennecke et al., "Principles of MicroRNA-Target Recognition," PLoS Biology, Mar. 2005, pp. 0404-0418, vol. 3, No. 3, e85.
Doench et al., "Specificity of microRNA target selection in translational repression," Genes & Development, 2004, pp. 1-8.
Furth et al., Anal Biochem 115, 1992, pp. 365-368, vol. 205.
Gold, Neuroscience, 1997, pp. 1153-1158, vol. 76.
Hofacker et al., Monatshefte f. Chemie, 1994, pp. 167-188, vol. 125.
International Search Report, PCT/IL2010/000575, date of mailing Mar. 15, 2011, 3 pages.
Jemal et al., "Cancer Statistics, 2008," CA Cancer J. Clin., Mar./Apr. 2008, pp. 71-96, vol. 58, No. 2.
Krützfeldt et al., "Silencing of microRNAs in vivo with 'antagomirs'," Nature 04303, Letters, 2005, pp. 1-5.
Rossi, "Receptor-targed SiRNAs", Nature Biotechnology 2005;23:682-4.
Song, et al., "Antibody mediated in vivo delivery of small interfering RNAs via cell-surface receptors", Nature Biotechnology 2005;23:709-17.
Soutschek et al., "Therapeutic silencing of an endogenous gene by systemic administration of modified siRNAs," Nature, Nov. 2004, pp. 173-178, vol. 432.
Tang et al., Nature, 1992, pp. 152-154, vol. 356.
Yekta et al., "MicroRNA-Directed Cleavage of *HOXB8* mRNA," Science, Apr. 2004, pp. 594-596, vol. 304.
Yi et al., "Morphogenesis in skin is governed by discrete sets of differentially expressed microRNAs," Nature Genetics—Advance Online Publication, Letters, 2006, pp. 1-7.
Porkka, et al., "MicroRNA Expression Profiling in Prostate Cancer", Cancer Research, 2007, vol. 16 (13), pp. 6130-6135.
International Search Report received in the parent International Patent Application No. PCT/IL2010/000575, dated Mar. 15, 2011.

* cited by examiner

*Primary Examiner* — Kimberly Chong
(74) *Attorney, Agent, or Firm* — Foley & Lardner LLP

(57) ABSTRACT

Described herein are compositions and methods for prognosis and treatment of prostate cancer patients. Specifically the invention relates to microRNA molecules associated with the prognosis of prostate cancer, as well as various nucleic acid molecules relating thereto or derived therefrom.

17 Claims, 13 Drawing Sheets

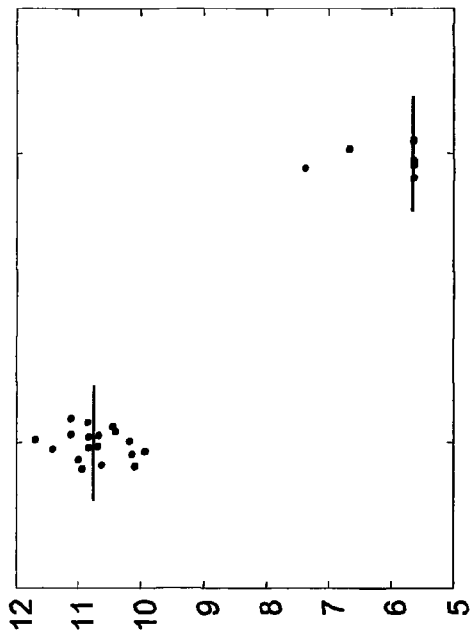
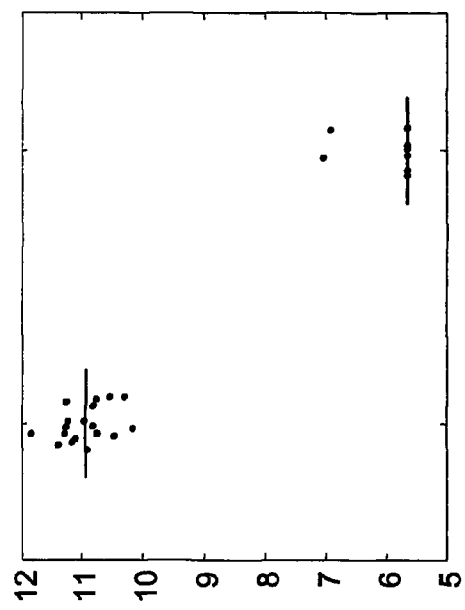
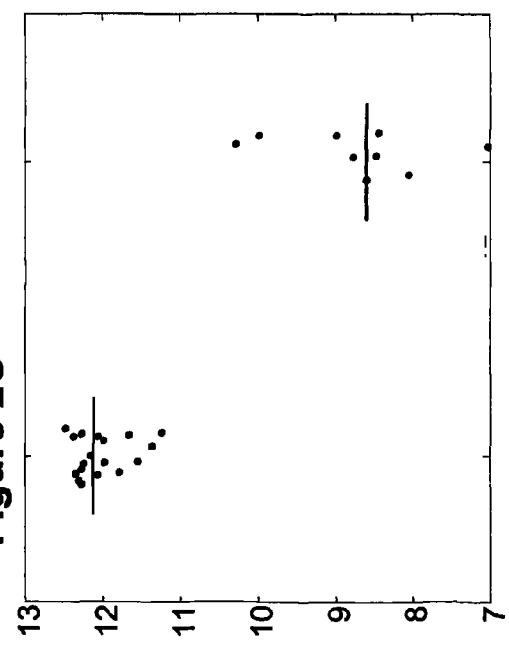

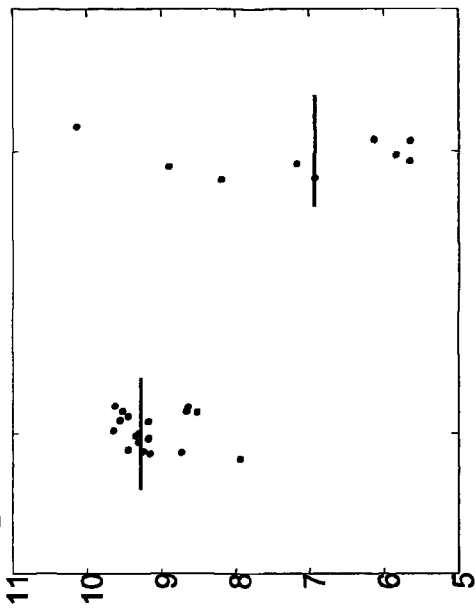
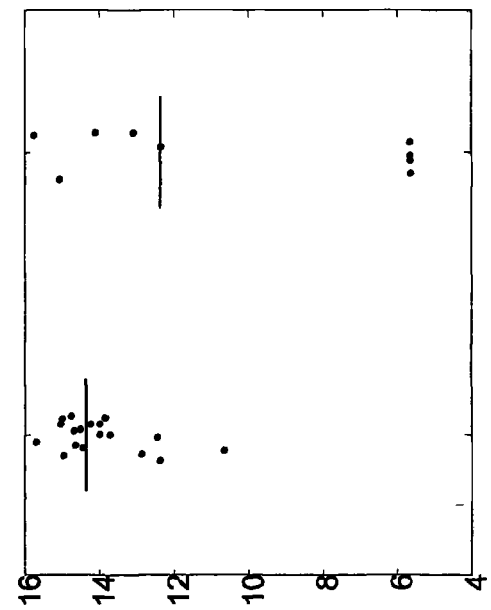
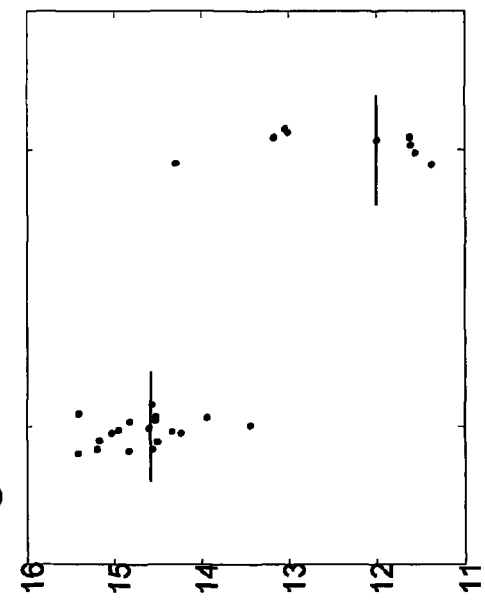
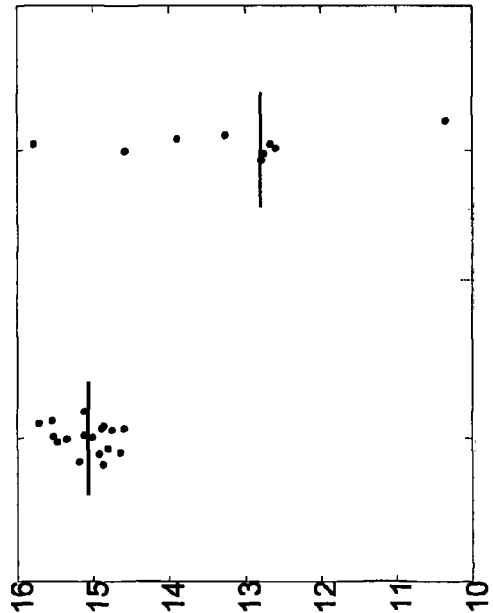

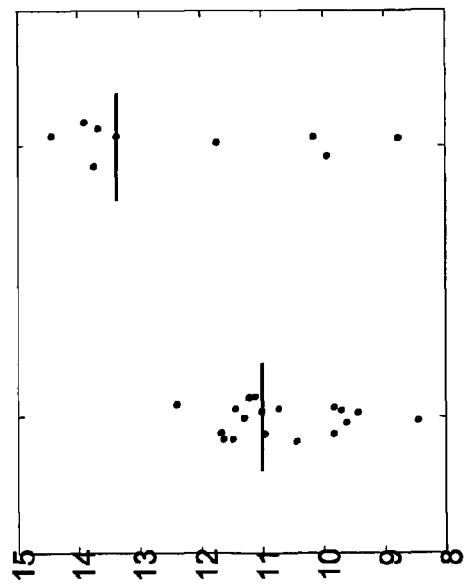
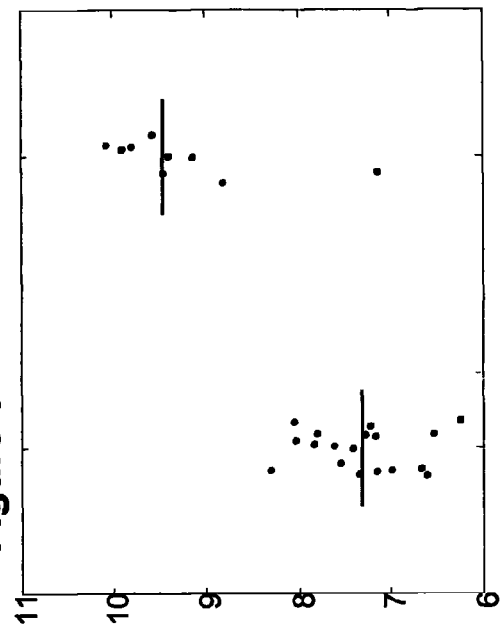
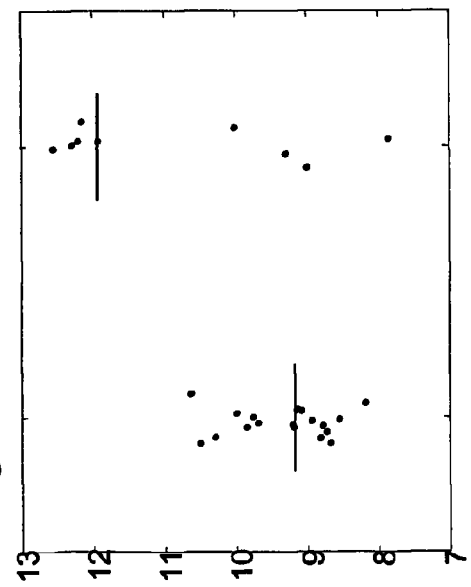
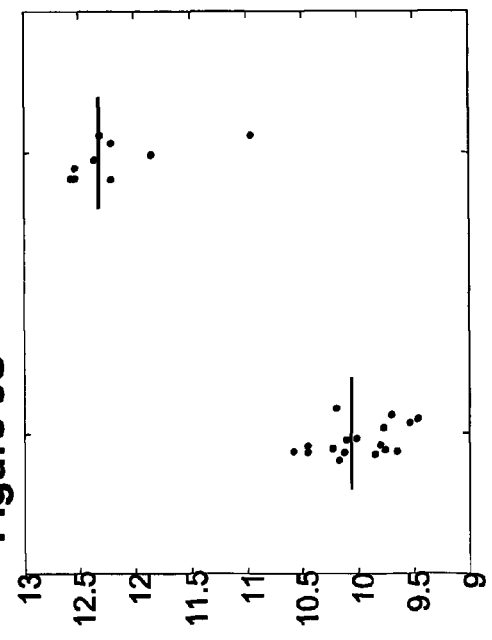
Figure 6A
Figure 6B
Figure 6C
Figure 6D

SEQUENCE LISTING

<160> NUMBER OF SEQ ID NOS: 101

<210> SEQ ID NO 1
<211> LENGTH: 22
<212> TYPE: RNA
<213> ORGANISM: Homo sapiens

<400> SEQUENCE: 1
uccuucauuc caccggaguc ug                                              22

<210> SEQ ID NO 2
<211> LENGTH: 22
<212> TYPE: RNA
<213> ORGANISM: Homo sapiens

<400> SEQUENCE: 2 uuugguccccc uucaaccagc ug                                             22

<210> SEQ ID NO 3

```
<211> LENGTH: 22
<212> TYPE: RNA
<213> ORGANISM: Homo sapiens

<400> SEQUENCE: 3
uuuggucccc uucaaccagc ua                                              22

<210> SEQ ID NO 4
<211> LENGTH: 22
<212> TYPE: RNA
<213> ORGANISM: Homo sapiens

<400> SEQUENCE: 4
ggugcagugc ugcaucucug gu                                              22

<210> SEQ ID NO 5
<211> LENGTH: 22
<212> TYPE: RNA
<213> ORGANISM: Homo sapiens

<400> SEQUENCE: 5
ggauuccugg aaauacuguu cu                                              22

<210> SEQ ID NO 6
<211> LENGTH: 23
<212> TYPE: RNA
<213> ORGANISM: Homo sapiens

<400> SEQUENCE: 6
guccaguuuu cccaggaauc ccu                                             23

<210> SEQ ID NO 7
<211> LENGTH: 21
<212> TYPE: RNA
<213> ORGANISM: Homo sapiens

<400> SEQUENCE: 7
ugagaugaag cacuguagcu c                                               21

<210> SEQ ID NO 8
<211> LENGTH: 23
<212> TYPE: RNA
<213> ORGANISM: Homo sapiens

<400> SEQUENCE: 8
uacccuguag aaccgaauuu gug                                             23

<210> SEQ ID NO 9
<211> LENGTH: 22
<212> TYPE: RNA
<213> ORGANISM: Homo sapiens

<400> SEQUENCE: 9
ugccugucua cacuugcugu gc                                              22

<210> SEQ ID NO 10
<211> LENGTH: 23
<212> TYPE: RNA
<213> ORGANISM: Homo sapiens

<400> SEQUENCE: 10
cccaguguuc agacuaccug uuc                                             23
```

```
<210> SEQ ID NO 11
<211> LENGTH: 23
<212> TYPE: RNA
<213> ORGANISM: Homo sapiens

<400> SEQUENCE: 11
cccaguguuu agacuaucug uuc                                               23

<210> SEQ ID NO 12
<211> LENGTH: 22
<212> TYPE: RNA
<213> ORGANISM: Homo sapiens

<400> SEQUENCE: 12
acagcaggca cagacaggca gu                                                22

<210> SEQ ID NO 13
<211> LENGTH: 22
<212> TYPE: RNA
<213> ORGANISM: Homo sapiens

<400> SEQUENCE: 13
acaguagucu gcacauuggu ua                                                22

<210> SEQ ID NO 14
<211> LENGTH: 22
<212> TYPE: RNA
<213> ORGANISM: Homo sapiens

<400> SEQUENCE: 14
ucccugagac ccuaacuugu ga                                                22

<210> SEQ ID NO 15
<211> LENGTH: 22
<212> TYPE: RNA
<213> ORGANISM: Homo sapiens

<400> SEQUENCE: 15
aacccguaga uccgaucuug ug                                                22

<210> SEQ ID NO 16
<211> LENGTH: 22
<212> TYPE: RNA
<213> ORGANISM: Homo sapiens

<400> SEQUENCE: 16
aacccguaga uccgaacuug ug                                                22

<210> SEQ ID NO 17
<211> LENGTH: 21
<212> TYPE: RNA
<213> ORGANISM: Homo sapiens

<400> SEQUENCE: 17
agcuacaucu ggcuacuggg u                                                 21

<210> SEQ ID NO 18
<211> LENGTH: 22
<212> TYPE: RNA
<213> ORGANISM: Homo sapiens

<400> SEQUENCE: 18
cagugcaaug uuaaaagggc au                                                22
```

```
<210> SEQ ID NO 19
<211> LENGTH: 24
<212> TYPE: RNA
<213> ORGANISM: Homo sapiens

<400> SEQUENCE: 19
ucccugagac ccuuuaaccu guga                                              24

<210> SEQ ID NO 20
<211> LENGTH: 21
<212> TYPE: RNA
<213> ORGANISM: Homo sapiens

<400> SEQUENCE: 20
gcaguccaug ggcauauaca c                                                 21

<210> SEQ ID NO 21
<211> LENGTH: 23
<212> TYPE: RNA
<213> ORGANISM: Homo sapiens

<400> SEQUENCE: 21
agcuacauug ucugcugggu uuc                                               23

<210> SEQ ID NO 22
<211> LENGTH: 21
<212> TYPE: RNA
<213> ORGANISM: Homo sapiens

<400> SEQUENCE: 22
ucagugcaug acagaacuug g                                                 21

<210> SEQ ID NO 23
<211> LENGTH: 22
<212> TYPE: RNA
<213> ORGANISM: Homo sapiens

<400> SEQUENCE: 23
uguaaacauc cucgacugga ag                                                22

<210> SEQ ID NO 24
<211> LENGTH: 21
<212> TYPE: RNA
<213> ORGANISM: Homo sapiens

<400> SEQUENCE: 24
uucaaguaau ucaggauagg u                                                 21

<210> SEQ ID NO 25
<211> LENGTH: 22
<212> TYPE: RNA
<213> ORGANISM: Homo sapiens

<400> SEQUENCE: 25
ugaccgauuu cuccuggugu uc                                                22

<210> SEQ ID NO 26
<211> LENGTH: 22
<212> TYPE: RNA
<213> ORGANISM: Homo sapiens

<400> SEQUENCE: 26
cugugcgugu gacagcggcu ga                                                22
```

```
<210> SEQ ID NO 27
<211> LENGTH: 23
<212> TYPE: RNA
<213> ORGANISM: Homo sapiens

<400> SEQUENCE: 27
aacauucauu gcugucggug ggu                                              23

<210> SEQ ID NO 28
<211> LENGTH: 22
<212> TYPE: RNA
<213> ORGANISM: Homo sapiens

<400> SEQUENCE: 28
uagcagcaca ucaugguuua ca                                               22

<210> SEQ ID NO 29
<211> LENGTH: 23
<212> TYPE: RNA
<213> ORGANISM: Homo sapiens

<400> SEQUENCE: 29
aaugacacga ucacucccgu uga                                              23

<210> SEQ ID NO 30
<211> LENGTH: 23
<212> TYPE: RNA
<213> ORGANISM: Homo sapiens

<400> SEQUENCE: 30
aacauucaac gcugucggug agu                                              23

<210> SEQ ID NO 31
<211> LENGTH: 22
<212> TYPE: RNA
<213> ORGANISM: Homo sapiens

<400> SEQUENCE: 31
uauggcacug guagaauuca cu                                               22

<210> SEQ ID NO 32
<211> LENGTH: 22
<212> TYPE: RNA
<213> ORGANISM: Homo sapiens

<400> SEQUENCE: 32
cagugcaaug augaaagggc au                                               22

<210> SEQ ID NO 33
<211> LENGTH: 22
<212> TYPE: RNA
<213> ORGANISM: Homo sapiens

<400> SEQUENCE: 33
ugucaguuug ucaaauaccc ca                                               22

<210> SEQ ID NO 34
<211> LENGTH: 24
<212> TYPE: RNA
<213> ORGANISM: Homo sapiens

<400> SEQUENCE: 34
```

```
uuuggcaaug guagaacuca cacu                                               24

<210> SEQ ID NO 35
<211> LENGTH: 21
<212> TYPE: RNA
<213> ORGANISM: Homo sapiens

<400> SEQUENCE: 35
uaaagugcug acagugcaga u                                                  21

<210> SEQ ID NO 36
<211> LENGTH: 22
<212> TYPE: RNA
<213> ORGANISM: Homo sapiens

<400> SEQUENCE: 36
uagcuuauca gacugauguu ga                                                 22

<210> SEQ ID NO 37
<211> LENGTH: 110
<212> TYPE: RNA
<213> ORGANISM: Homo sapiens

<400> SEQUENCE: 37
aaagauccuc agacaaucca ugugcuucuc uuguccuuca uuccaccgga gucugucuca        60
uacccaacca gauuucagug gagugaaguu caggaggcau ggagcugaca                  110

<210> SEQ ID NO 38
<211> LENGTH: 88
<212> TYPE: RNA
<213> ORGANISM: Homo sapiens

<400> SEQUENCE: 38
acaaugcuuu gcuagagcug guaaaaugga accaaaucgc cucuucaaug gauuuggucc        60
ccuucaacca gcuguagcua ugcauuga                                           88

<210> SEQ ID NO 39
<211> LENGTH: 119
<212> TYPE: RNA
<213> ORGANISM: Homo sapiens

<400> SEQUENCE: 39
ccucagaaga aagaugcccc cugcucuggc uggucaaacg gaaccaaguc cgucuuccug        60
agagguuugg uccccuucaa ccagcuacag cagggcuggc aaugcccagu ccuuggaga       119

<210> SEQ ID NO 40
<211> LENGTH: 106
<212> TYPE: RNA
<213> ORGANISM: Homo sapiens

<400> SEQUENCE: 40
gcgcagcgcc cugucuccca gccugaggug cagcugcuca ucucggguca guugggaguc        60
ugagaugaag cacuguagcu caggaagaga gaaguuguuc ugcagc                      106

<210> SEQ ID NO 41
<211> LENGTH: 88
<212> TYPE: RNA
<213> ORGANISM: Homo sapiens

<400> SEQUENCE: 41
caccuugucc ucacggucca guuucccag gaaucccuua gaugcuaaga uggggauucc        60
```
uggaaauacu guucuugagg ucaugguu                                              88

<210> SEQ ID NO 42
<211> LENGTH: 110
<212> TYPE: RNA
<213> ORGANISM: Homo sapiens

<400> SEQUENCE: 42
ccagagguug uaacguuguc uauauauacc cuguagaacc gaauuugugu gguauccgua           60
uagucacaga uucgauucua ggggaauaua uggucgaugc aaaaacuuca                     110

<210> SEQ ID NO 43
<211> LENGTH: 110
<212> TYPE: RNA
<213> ORGANISM: Homo sapiens

<400> SEQUENCE: 43
ggccuggcug gacagaguug ucaugugucu gccugucuac acuugcugug cagaacaucc           60
gcucaccugu acagcaggca cagacaggca gucaugac aacccagccu                      110

<210> SEQ ID NO 44
<211> LENGTH: 71
<212> TYPE: RNA
<213> ORGANISM: Homo sapiens

<400> SEQUENCE: 44
gccaacccag uguucagacu accuguucag gaggcucuca auguguacag uagucugcac           60
auugguuagg c                                                                71

<210> SEQ ID NO 45
<211> LENGTH: 110
<212> TYPE: RNA
<213> ORGANISM: Homo sapiens

<400> SEQUENCE: 45
ccagaggaca ccuccacucc gucuacccag uguuuagacu aucuguucag gacucccaaa           60
uuguacagua gucugcacau ugguuaggcu gggcuggguu agacccucgg                     110

<210> SEQ ID NO 46
<211> LENGTH: 110
<212> TYPE: RNA
<213> ORGANISM: Homo sapiens

<400> SEQUENCE: 46
ggccuggcug gacagaguug ucaugugucu gccugucuac acuugcugug cagaacaucc           60
gcucaccugu acagcaggca cagacaggca gucaugac aacccagccu                      110

<210> SEQ ID NO 47
<211> LENGTH: 88
<212> TYPE: RNA
<213> ORGANISM: Homo sapiens

<400> SEQUENCE: 47
ugcgcuccuc ucagucccug agacccuaac uugugauguu uaccguuuaa auccacgggu           60
uaggcucuug ggagcugcga gucgugcu                                              88

<210> SEQ ID NO 48
<211> LENGTH: 81
<212> TYPE: RNA

-continued

<213> ORGANISM: Homo sapiens

<400> SEQUENCE: 48
cccauuggca uaaacccgua gauccgaucu ugguguaag uggaccgcac aagcucgcuu    60
cuaugggucu gugucagugu g                                             81

<210> SEQ ID NO 49
<211> LENGTH: 80
<212> TYPE: RNA
<213> ORGANISM: Homo sapiens

<400> SEQUENCE: 49
ccuguugcca caaacccgua gauccgaacu uguguauua guccgcacaa gcuuguaucu    60
auagguaugu gucuguuagg                                               80

<210> SEQ ID NO 50
<211> LENGTH: 110
<212> TYPE: RNA
<213> ORGANISM: Homo sapiens

<400> SEQUENCE: 50
gcugcuggaa gguguaggua cccucaaugg cucaguagcc aguguagauc cugucuuucg    60
uaaucagcag cuacaucugg cuacgggguc ucgauggca ucuucuagcu               110

<210> SEQ ID NO 51
<211> LENGTH: 89
<212> TYPE: RNA
<213> ORGANISM: Homo sapiens

<400> SEQUENCE: 51
ugcugcuggc cagagcucuu uucacauugu gcuacugucu gcaccuguca cuagcagugc    60
aauguuaaaa gggcauuggc cguguagug                                     89

<210> SEQ ID NO 52
<211> LENGTH: 86
<212> TYPE: RNA
<213> ORGANISM: Homo sapiens

<400> SEQUENCE: 52
ugccagucuc uaggucccug agacccuuua accgugagg acaccaggg ucacagguga    60 gguucuuggg agccuggcgu cuggcc                                        86

<210> SEQ ID NO 53
<211> LENGTH: 96
<212> TYPE: RNA
<213> ORGANISM: Homo sapiens

<400> SEQUENCE: 53
ucccuggcgu gagguaugu gccuuuggac uacaucgugg aagccagcac caugcagucc    60
augggcauau acacuugccu caaggccuau gucauc                             96

<210> SEQ ID NO 54
<211> LENGTH: 110
<212> TYPE: RNA
<213> ORGANISM: Homo sapiens

<400> SEQUENCE: 54
ugaacaucca ggucuggggc augaaccugg cauacaaugu agauuucugu guucguuagg    60
caacagcuac auugcugcu ggguuucagg cuaccuggaa acauguucuc               110

<210> SEQ ID NO 55
<211> LENGTH: 87
<212> TYPE: RNA
<213> ORGANISM: Homo sapiens

<400> SEQUENCE: 55 ugucccccc ggcccagguu cugugauaca cuccgacucg ggcucuggag cagucagugc    60
augacagaac uugggcccgg aaggacc                                      87

<210> SEQ ID NO 56
<211> LENGTH: 71
<212> TYPE: RNA
<213> ORGANISM: Homo sapiens

<400> SEQUENCE: 56
gcgacuguaa acauccucga cuggaagcug ugaagccaca gaugggcuuu cagucggaug    60
uuugcagcug c                                                       71

<210> SEQ ID NO 57
<211> LENGTH: 77
<212> TYPE: RNA
<213> ORGANISM: Homo sapiens

<400> SEQUENCE: 57
ccgggaccca guucaaguaa uucaggauag guugugugcu guccagccug uucuccauua    60
cuuggcucgg ggaccgg                                                 77

<210> SEQ ID NO 58
<211> LENGTH: 88
<212> TYPE: RNA
<213> ORGANISM: Homo sapiens

<400> SEQUENCE: 58
aucucuuaca caggcugacc gauuucuccu gguguucaga gucuguuuuu gucuagcacc    60
auuugaaauc gguuaugaug uaggggga                                     88

<210> SEQ ID NO 59
<211> LENGTH: 110
<212> TYPE: RNA
<213> ORGANISM: Homo sapiens

<400> SEQUENCE: 59
acccggcagu gccuccaggc gcagggcagc cccugcccac cgcacacugc gcugccccag    60
acccacugug cgugugacag cggcugaucu gugccugggc agcgcgaccc              110

<210> SEQ ID NO 60
<211> LENGTH: 110
<212> TYPE: RNA
<213> ORGANISM: Homo sapiens

<400> SEQUENCE: 60
ccugugcaga gauuauuuuu uaaaagguca caaucaacau ucauugcugu cggugggüug    60 aacugugugg acaagcucac ugaacaauga augcaacugu ggccccgcuu              110

<210> SEQ ID NO 61
<211> LENGTH: 89
<212> TYPE: RNA
<213> ORGANISM: Homo sapiens

```
<400> SEQUENCE: 61
cugauggcug cacucaacau ucauugcugu cgguggguuu gagucugaau caacucacug    60
aucaaugaau gcaaacugcg gaccaaaca                                      89

<210> SEQ ID NO 62
<211> LENGTH: 98
<212> TYPE: RNA
<213> ORGANISM: Homo sapiens

<400> SEQUENCE: 62
uugaggccuu aaaguacugu agcagcacau cauggguuac augcuacagu caagaugcga    60
aucauuauuu gcugcucuag aaauuuaagg aaauucau                            98

<210> SEQ ID NO 63
<211> LENGTH: 87
<212> TYPE: RNA
<213> ORGANISM: Homo sapiens

<400> SEQUENCE: 63
gaaagcgcuu uggaaugaca cgaucacucc cguugagugg gcacccgaga agccaucggg    60
aaugucgugu ccgcccagug cucuuuc                                        87

<210> SEQ ID NO 64
<211> LENGTH: 110
<212> TYPE: RNA
<213> ORGANISM: Homo sapiens

<400> SEQUENCE: 64
agaagggcua ucaggccagc cuucagagga cuccaaggaa cauucaacgc ugucggugag    60
uuugggauuu gaaaaaacca cugaccguug acuuaccuu ggguccuua                110

<210> SEQ ID NO 65
<211> LENGTH: 110
<212> TYPE: RNA
<213> ORGANISM: Homo sapiens

<400> SEQUENCE: 65
ccgcagagug ugacuccugu ucuguguaug gcacugguag aauucacugu gaacagucuc    60
agucagugaa uuaccgaagg gccauaaaca gagcagagac agauccacga              110

<210> SEQ ID NO 66
<211> LENGTH: 82
<212> TYPE: RNA
<213> ORGANISM: Homo sapiens

<400> SEQUENCE: 66
ggccugcccg acacucuuuc ccuguugcac uacuauaggc cgcugggaag cagugcaaug    60
augaaagggc aucggucagg uc                                             82

<210> SEQ ID NO 67
<211> LENGTH: 110
<212> TYPE: RNA
<213> ORGANISM: Homo sapiens

<400> SEQUENCE: 67
ccuggccucc ugcagugcca cgcuccgugu auuugacaag cugaguugga cacuccaugu    60
gguagagugu caguuuguca aauaccccaa gugcggcaca ugcuuaccag              110
```

```
<210> SEQ ID NO 68
<211> LENGTH: 110
<212> TYPE: RNA
<213> ORGANISM: Homo sapiens

<400> SEQUENCE: 68
gagcugcuug ccuccccccg uuuuuggcaa ugguagaacu cacacuggug agguaacagg      60
auccgguggu ucuagacuug ccaacuaugg ggcgaggacu cagccggcac                110

<210> SEQ ID NO 69
<211> LENGTH: 82
<212> TYPE: RNA
<213> ORGANISM: Homo sapiens

<400> SEQUENCE: 69
ccugccgggg cuaaagugcu gacagugcag auaguggucc ucccgugcu accgcacugu       60 gggguacuugc ugcuccagca gg                                              82

<210> SEQ ID NO 70
<211> LENGTH: 72
<212> TYPE: RNA
<213> ORGANISM: Homo sapiens

<400> SEQUENCE: 70
ugucggguag cuuaucagac ugauguugac uguugaaucu cauggcaaca ccagucgaug      60
ggcugucuga ca                                                         72

<210> SEQ ID NO 71
<211> LENGTH: 21
<212> TYPE: RNA
<213> ORGANISM: Homo sapiens

<400> SEQUENCE: 71
aggcaagaug cuggcauagc u                                               21

<210> SEQ ID NO 72
<211> LENGTH: 71
<212> TYPE: RNA
<213> ORGANISM: Homo sapiens

<400> SEQUENCE: 72
ggagaggagg caagaugcug gcauagcugu ugaacuggga accugcuaug ccaacauauu      60
gccaucuuuc c                                                          71

<210> SEQ ID NO 73
<211> LENGTH: 22
<212> TYPE: RNA
<213> ORGANISM: Homo sapiens

<400> SEQUENCE: 73
caagcucgcu ucuauggguc ug                                              22

<210> SEQ ID NO 74
<211> LENGTH: 81
<212> TYPE: RNA
<213> ORGANISM: Homo sapiens

<400> SEQUENCE: 74
cccauuggca uaaacccgua gauccgaucu uguggugaag uggaccgcac aagcucgcuu      60
cuaugggucu gugucagugu g                                               81
```

```
<210> SEQ ID NO 75
<211> LENGTH: 19
<212> TYPE: RNA
<213> ORGANISM: Homo sapiens

<400> SEQUENCE: 75
accgugcaaa gguagcaua                                                19

<210> SEQ ID NO 76
<211> LENGTH: 44
<212> TYPE: RNA
<213> ORGANISM: Homo sapiens

<400> SEQUENCE: 76
uauguucaac ggccaugguga uccugaccgu gcaaagguag caua                   44

<210> SEQ ID NO 77
<211> LENGTH: 19
<212> TYPE: RNA
<213> ORGANISM: Homo sapiens

<400> SEQUENCE: 77
uaaaaggaac ucggcaaau                                                19

<210> SEQ ID NO 78
<211> LENGTH: 66
<212> TYPE: RNA
<213> ORGANISM: Homo sapiens

<400> SEQUENCE: 78
acaggcaugc ucuaaggaaa gguuaaaaaa aauuaaaagg aacucggcaa auuuuacccu   60
gccugu                                                              66

<210> SEQ ID NO 79
<211> LENGTH: 23
<212> TYPE: RNA
<213> ORGANISM: Homo sapiens

<400> SEQUENCE: 79
uaaggugcau cuagugcagu uag                                           23

<210> SEQ ID NO 80
<211> LENGTH: 71
<212> TYPE: RNA
<213> ORGANISM: Homo sapiens

<400> SEQUENCE: 80
uguguuaagg ugcaucuagu gcaguuagug aagcagcuua gaaucuacug cccuaaaugc   60
cccuucuggc a                                                        71

<210> SEQ ID NO 81
<211> LENGTH: 21
<212> TYPE: RNA
<213> ORGANISM: Homo sapiens

<400> SEQUENCE: 81
uaggucaagg uguagcccau a                                             21

<210> SEQ ID NO 82
<211> LENGTH: 128
<212> TYPE: RNA
<213> ORGANISM: Homo sapiens
```

```
<400> SEQUENCE: 82
cauaaaaacu uuaggucaag guguagccca uaagguggca agaaauggga acguuucua        60 cauccagaaa aaugucgcga caaccguuau gaaaucuaag ggcucaagga ggauuuagca       120
auaaauug                                                                128

<210> SEQ ID NO 83
<211> LENGTH: 21
<212> TYPE: RNA
<213> ORGANISM: Homo sapiens

<400> SEQUENCE: 83
cauccuagcc cuaagucugg c                                                  21

<210> SEQ ID NO 84
<211> LENGTH: 119
<212> TYPE: RNA
<213> ORGANISM: Homo sapiens

<400> SEQUENCE: 84
uccuuuuacc ccuaccauga gcccuacaaa caacuaaccu gccacuaaua guuaugucau        60
cccucuuauu aaucaucauc cuagcccuaa gucuggccua ugagugacua caaaaagga       119

<210> SEQ ID NO 85
<211> LENGTH: 23
<212> TYPE: RNA
<213> ORGANISM: Homo sapiens

<400> SEQUENCE: 85
uaaggugcau cuagugcaga uag                                                23

<210> SEQ ID NO 86
<211> LENGTH: 71
<212> TYPE: RNA
<213> ORGANISM: Homo sapiens

<400> SEQUENCE: 86
uguucuaagg ugcaucuagu gcagauagug aaguagauua gcaucuacug cccuaagugc        60
uccuucuggc a                                                             71

<210> SEQ ID NO 87
<211> LENGTH: 22
<212> TYPE: RNA
<213> ORGANISM: Homo sapiens

<400> SEQUENCE: 87
aaaccguuac cauuacugag uu                                                 22

<210> SEQ ID NO 88
<211> LENGTH: 72
<212> TYPE: RNA
<213> ORGANISM: Homo sapiens

<400> SEQUENCE: 88
cuugggaaug gcaaggaaac cguuaccauu acugaguuua guaaugguaa igguucucuu        60 gcuauaccca ga                                                            72

<210> SEQ ID NO 89
<211> LENGTH: 22
<212> TYPE: RNA
```

```
<213> ORGANISM: Homo sapiens

<400> SEQUENCE: 89
ugugccaugu uggugugcug ca                                              22

<210> SEQ ID NO 90
<211> LENGTH: 86
<212> TYPE: RNA
<213> ORGANISM: Homo sapiens

<400> SEQUENCE: 90
uaaguuuuag ggugcaugug cacaacgugc agguuuguua cauauguaua caugugccau     60
guuggugugc ugcacccguu aacuug                                          86

<210> SEQ ID NO 91
<211> LENGTH: 89
<212> TYPE: RNA
<213> ORGANISM: Homo sapiens

<400> SEQUENCE: 91
uguuaaucca acacaggcau gcucuaagga aauauuacaa aaaguaaaag gaacucggca     60
aaucuuaccc caccuguuua ccaaaaaca                                       89

<210> SEQ ID NO 92
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cacaaguucg gaucuacggg uu                                              22

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
aucugcacug ucagcacuuu a                                               21

<210> SEQ ID NO 94
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
acucaccgac agcguugaau guu                                             23

<210> SEQ ID NO 95
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
```
acccaccgac agcaaugaau guu                                          23

<210> SEQ ID NO 96
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
cagcugcuuu ugggauuccg uug                                          23

<210> SEQ ID NO 97
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
ucaacaucag ucugauaagc ua                                           22

<210> SEQ ID NO 98
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
ucagccgcug ucacacgcac ag                                           22

<210> SEQ ID NO 99
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
cacaaauucg guucuacagg gua                                          23

<210> SEQ ID NO 100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
acauacuccu uucucagagu cca                                          23

<210> SEQ ID NO 101
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 101
gcaatgctag ctattgcttg ctattaaaaa                                              30
```

COMPOSITIONS AND METHODS FOR PROGNOSIS AND TREATMENT OF PROSTATE CANCER

CROSS-REFERENCE TO RELATED PATENT APPLICATIONS

This application is the U.S. National Phase of PCT/IL2010/000575, filed Jul. 20, 2010, which claims priority from U.S. Provisional Application Nos. 61/235,011, filed Aug. 19, 2009, all of which are incorporated herein by reference in entirety.

SEQUENCE LISTING

The instant application contains a Sequence Listing which has been submitted in ASCII format via EFS-Web and is hereby incorporated by reference in its entirety. Said ASCII copy, created on May 22, 2012, is named 91394134.txt and is 18,962 bytes in size.

FIELD OF THE INVENTION

The invention relates to compositions and methods for prognosis and treatment of prostate cancer. Specifically the invention relates to microRNA molecules associated with the prognosis and treatment of prostate cancer, as well as various nucleic acid molecules relating thereto or derived therefrom.

BACKGROUND OF THE INVENTION

Prostate cancer is the most common noncutaneous cancer in males and the second most common cause of cancer-related death in men in the United States (Jemal et al. (2008) CA Cancer J. Clin. 58:71-96). The American Cancer Society estimates that in 2009, 92,280 new cases of prostate cancer will be diagnosed and 27,360 men will die of prostate cancer. The incidence of prostate cancer diagnosis in men exceeds 1 in 6, and the death rate due to prostate cancer is approximately 1 in 35. Standard treatment of advanced and/or metastatic prostate cancer includes androgen suppression, cytotoxic chemotherapy, and radiation. These treatment modalities carry significant side effects, and treatment regimes (and consequently likelihood of success) are far more limited for hormone-refractory prostate tumors than hormone-responsive tumors. For metastatic prostate cancer, no form of therapy is curative, and thus this represents a terminal diagnosis. Surgical approaches and radiation, typically in combination with hormone therapy, may be used for intermediate-stage tumors; however, again, these modalities carry significant risk of undesirable side effects such as incontinence and/or impotence. For early-stage tumors, standard approaches consist of surgery, radiation (which may be combined with hormone therapy) or watchful waiting. With watchful waiting, consensus guidelines related to its implementation are lacking, changes in clinical parameters with time lead to frequent repetitive biopsies, and with the knowledge that they have confirmed prostate cancer patients experience high levels of anxiety. All of these factors contribute to a channeling of patients into eventual treatment with surgery or radiation.

microRNAs (miRNAs, miRs) are endogenous non-coding small RNA's that interfere with the translation of coding messenger RNAs (mRNAs) in a sequence-specific manner, playing a critical role in the control of gene expression during development and tissue homeostasis (Yi et al., Nat Genet 2006; 38:356-362). Certain miRNAs have been shown to be deregulated in human cancer, and their specific over- or under-expression has been shown to correlate with particular tumor types (Calin and Croce, Nat Rev Cancer 2006; 6:857-866), as well as to predict patient outcome (Yu et al., Cancer Cell 2008; 13:48-57). In some cases miRNA over-expression results in reduced expression of tumor suppressor genes, while loss of miRNA expression often leads to oncogene activation.

Significant associations have been demonstrated between expression of miRNA signatures and clinical outcome of lung adenocarcinoma, chronic lymphocytic leukemia, breast and pancreatic cancers.

Prognosis and staging of prostate cancer is an important tool in weighing the efficacy and cost-effectiveness of alternative treatments. Any improvement in prognostic tools will enable better treatment of those in need, increasing their chances of a full cure and/or increasing their life expectancy, as well as quality of life. While a mere shift in the threshold for decisions on treatment may assign more patients to seemingly life-extending treatment regimens, these carry the increased risk of unpleasant and potentially life-threatening side-effects for patients who would not benefit from the treatment, or for those who should be assigned alternative protocols or none at all.

The prognosis for prostate is influenced by the stage of the disease. Surgery, when performed as part of a multimodality therapy with cytotoxic chemotherapy and radiation therapy, can be effective treatment, but only in the rare event of an early stage diagnosis. Accordingly, there is a great need for more sensitive and accurate methods for the prognosis of prostate cancer in a human to determine whether or not such cancer will become aggressive (will metastasize).

Thus, there exists a need for identification of biomarkers that can be used as prognostic indicators for prostate cancer.

Better treatment of prostate cancer is also needed. In particular, agents that prevent prostate cancer metastasis are needed.

SUMMARY OF THE INVENTION

According to some aspects of the present invention, altered expression levels of SEQ ID NO: 1-91 or any combinations thereof, are indicative of prostate cancer prognosis: life expectancy of the patient, expected recurrence-free survival, and risk of recurrence of prostate metastases.

According to one aspect of the invention, a method for determining a prognosis for prostate cancer in a subject is provided, the method comprising:
 (a) obtaining a biological sample from the subject;
 (b) determining the expression level of a nucleic acid sequence selected from the group consisting of SEQ ID NOS: 1-91 and sequences at least about 80% identical thereto from said sample; and
 (c) comparing said expression level to a threshold expression level,
  wherein the level of any of SEQ ID NOS: 1-91 and sequences at least about 80% identical thereto compared to said threshold expression level is indicative of the prognosis of said subject.

In some embodiments, the nucleic acid sequence is selected from the group consisting of SEQ ID NOS: 1-25, 37-58, 71-74 and sequences at least about 80% identical thereto, and an increased expression level of any of said nucleic acid sequence compared to the threshold expression level is indicative of good prognosis of said subject. In other embodiments, the nucleic acid sequence is selected from the group consisting of SEQ ID NOS: 26-36, 59-70, 75-91 and sequences at least about 80% identical thereto, and an increased expression level of any of said nucleic acid sequence compared to the threshold expression level is indicative of poor prognosis of said subject.

In certain embodiments, the subject is a human.

In certain embodiments, the method is used to determine a course of treatment of the subject.

In certain embodiments the biological sample obtained from the subject is selected from the group consisting of a bodily fluid, a cell line or a tissue sample. In certain embodiments the tissue is a fresh, frozen, fixed, wax-embedded or formalin-fixed, paraffin-embedded (FFPE) tissue.

In certain embodiments said tissue is a prostate cancer tissue.

According to some embodiments, the expression levels are determined by method selected from the group consisting of nucleic acid hybridization, nucleic acid amplification, or a combination thereof. According to some embodiments, the nucleic acid hybridization is performed using a solid-phase nucleic acid biochip array or in situ hybridization.

According to other embodiments, the nucleic acid amplification method is real-time PCR. According to some embodiments, the PCR method comprises forward and reverse primers. According to some embodiments the forward primer is partially complementary to SEQ ID NOS: 1-91, to a fragment thereof or to a sequence at least about 80% identical thereto. According to some embodiments, the real-time PCR method further comprises a probe. According to some embodiments, the probe is complementary to SEQ ID NOS: 1-91, to a fragment thereof or to a sequence at least about 80% identical thereto. According to some embodiments, the probe is a general probe. According to some embodiments, the general probe is homologues to the linker part of the consensus sequence and the polyA sequence.

The invention further provides a kit for prognosis of prostate cancer, said kit comprising forward and reverse primers and a probe. According to some embodiments the forward primer is partially complementary to SEQ ID NOS: 1-91, to a fragment thereof or to a sequence at least about 80% identical thereto. According to some embodiments said kit comprising a probe comprising a nucleic acid sequence that is complementary to a sequence selected from SEQ ID NO: 1-91, to a fragment thereof or to a sequence at least about 80% identical thereto. According to some embodiments, the probe is a general probe. According to some embodiments, the general probe is homologues to the linker part of the consensus sequence and the polyA sequence.

According to some embodiments, said kit comprises reagents for performing in situ hybridization analysis. According to some embodiments, said kit comprises reagents for performing solid-phase nucleic acid biochip array.

A method of preventing or treating prostate cancer in a subject in need thereof is also provided. The method may comprise administering to the subject an effective amount of a composition comprising a nucleic acid sequence selected from the group consisting of a complementary sequence of SEQ ID NOS: 26-36, 59-70, 75-91 and a sequence at least about 80% identical thereto.

The method may comprise administering to the subject an effective amount of a composition comprising a nucleic acid sequence selected from the group consisting of SEQ ID NOS: 1-25, 37-58, 71-74, and a sequence having at least 80% identity thereto. According to some embodiments the nucleic acid comprises a modified base.

According to some embodiments, the administration comprises intratumoral administration, chemoemobilization, subcutaneous administration or intravenous administration.

According to other aspects, a method is provided for inhibiting the growth or viability of prostate cancer cells comprising increasing, in said cells, the expression level of a nucleic acid sequence selected from the group consisting of SEQ ID NOS: 1-25, 37-58, 71-74 and sequences having at least 80% identity thereto.

According to some aspects, a method is provided for inhibiting the growth or viability of prostate cancer cells comprising inhibiting, in said cells, the expression level of a nucleic acid sequence selected from the group consisting of SEQ ID NOS: 26-36, 59-70, 75-91 and sequences having at least 80% identity thereto.

A method for inhibiting prostate cancer metastasis in a subject in need thereof is also provided. The method may comprise administering to the subject an effective amount of a composition comprising a nucleic acid sequence selected from the group consisting of a complementary sequence of SEQ ID NOS: 26-36, 59-70, 75-91 and a sequence at least about 80% identical thereto.

The method may comprise administering to the subject an effective amount of a composition comprising a nucleic acid sequence selected from the group consisting of SEQ ID NOS: 1-25, 37-58, 71-74, and a sequence having at least 80% identity thereto.

The use of a nucleic acid comprising a nucleic acid sequence selected from the group consisting of:
(a) SEQ ID NOS: 1-25, 37-58, 71-74,
(b) a sequence that is complementary to SEQ ID NOS: 26-36, 59-70, 75-91; and
(c) a sequence at least about 80% identical to (a) or (b),
for the manufacture of a medicament for the treatment or prevention of prostate cancer, is also provided.

These and other embodiments of the present invention will become apparent in conjunction with the figures, description and claims that follow.

BRIEF DESCRIPTION OF THE DRAWINGS

FIGS. 2A-D are dot plot presentations comparing the group of patients with primary prostate cancer (the left box) with the group of patients with metastatic prostate cancer (the right box), with regard to expression (in $\log_2$(fluorescence units)) of the following miRs:

FIG. 2A: hsa-miR-133a (SEQ ID NO: 2), (P-value 1.9e-019 and fold change of 39.5)

FIG. 2B: hsa-miR-133b (SEQ ID NO: 3), (P-value 5.9e-018 and fold change of 34.8)

FIG. 2C: hsa-miR-143* (SEQ ID NO: 4), (P-value 1.7e-012 and fold change of 11.4)

and FIG. 2D: hsa-miR-31 (SEQ ID NO: 71), (P-value 0.000023 and fold change of 8.2). The horizontal lines indicate the median values.

FIG. 3A: hsa-miR-145* (SEQ ID NO: 5), (P-value 3.4e-013 and fold change of 8.i)

FIG. 3B: hsa-miR-143 (SEQ ID NO: 7), (P-value 7.9e-015 and fold change of 7.8)

FIG. 3C: hsa-miR-145 (SEQ ID NO: 6), (P-value 4.9e-014 and fold change of 6.9) and FIG. 3D: hsa-miR-221 (SEQ ID NO: 21), (P-value 2.3e-007 and fold change of 6.3). The horizontal lines indicate the median values.

FIGS. 4A-D are dot plot presentations comparing the group of patients with primary prostate cancer (the left box) with the group of patients with metastatic prostate cancer (the right box), with regard to expression (in $\log_2$(fluorescence units)) of the following miRs:

FIG. 4A: hsa-miR-222 (SEQ ID NO: 17), (P-value 3.2e-008 and fold change of 6.0)

FIG. 4B: hsa-miR-99a* (SEQ ID NO: 73), (P-value 0.000047 and fold change of 5.1)

FIG. 4C: hsa-miR-99a (SEQ ID NO: 15), (P-value 0.000022 and fold change of 4.9)

and FIG. 4D: hsa-miR-205 (SEQ ID NO: 1), (P-value 0.003266 and fold change of 4.0). The horizontal lines indicate the median values.

FIG. 5A: hsa-miR-125b (SEQ ID NO: 14), (P-value 0.000002 and fold change of 3.5)

FIG. 5B: hsa-miR-100 (SEQ ID NO: 16), (P-value 1.5e-007 and fold change of 3.4)

FIG. 5C: hsa-miR-10b (SEQ ID NO: 8), (P-value 0.005627 and fold change of 3.3) and FIG. 5D: hsa-miR-210 (SEQ ID NO: 26), (P-value 1.3e-008 and fold change of 10.9). The horizontal lines indicate the median values.

FIGS. 6A-D are dot plot presentations comparing the group of patients, with primary prostate cancer (the left box) with the group of patients with metastatic prostate cancer (the right box), with regard to expression (in $\log_2$(fluorescence units)) of the following miRs:

FIG. 6A: hsa-miR-1973 (SEQ ID NO: 75), (P-value 0.004619 and fold change of 6.8)

FIG. 6B: MID-19962 (SEQ ID NO: 77), (P-value 0.017396 and fold change of 5.2)

FIG. 6C: hsa-miR-425 (SEQ ID NO: 29), (P-value 5.9e-013 and fold change of 4.8) and FIG. 6D: hsa-miR-18b (SEQ ID NO: 27), (P-value 3.2e-007 and fold change of 4.4). The horizontal lines indicate the median values.

FIG. 7A: MID-20524 (SEQ ID NO: 81), (P-value 0.003769 and fold change of 44)

FIG. 7B: MID-17375 (SEQ ID NO: 83), (P-value 0.024966 and fold change of 4.3)

FIG. 7C: hsa-miR-18a (SEQ ID NO: 85), (P-value 3.9e-009 and fold change of 4.6)

and FIG. 7D: hsa-miR-183 (SEQ ID NO: 31), (P-value 0.000001 and fold change of 3.5). The horizontal lines indicate the median values.

FIG. 8A: hsa-miR-181b (SEQ ID NO: 27), (P-value 7.0e-009 and fold change of 3.4)

FIG. 8B: hsa-miR-181a (SEQ ID NO: 30), (P-value 9.8e-009 and fold change of 3.3)

FIG. 8C: hsa-miR-15b (SEQ ID NO: 28), (P-value 2.8e-009 and fold change 6f 3.3)

and FIG. 8D: hsa-miR-106b (SEQ ID NO: 35), (P-value 8.2e-010 and fold change of 3.3). The horizontal lines indicate the median values.

The diagonal line represents a possible binary classification such that patient's below it may be treated aggressively.

Figure 11:
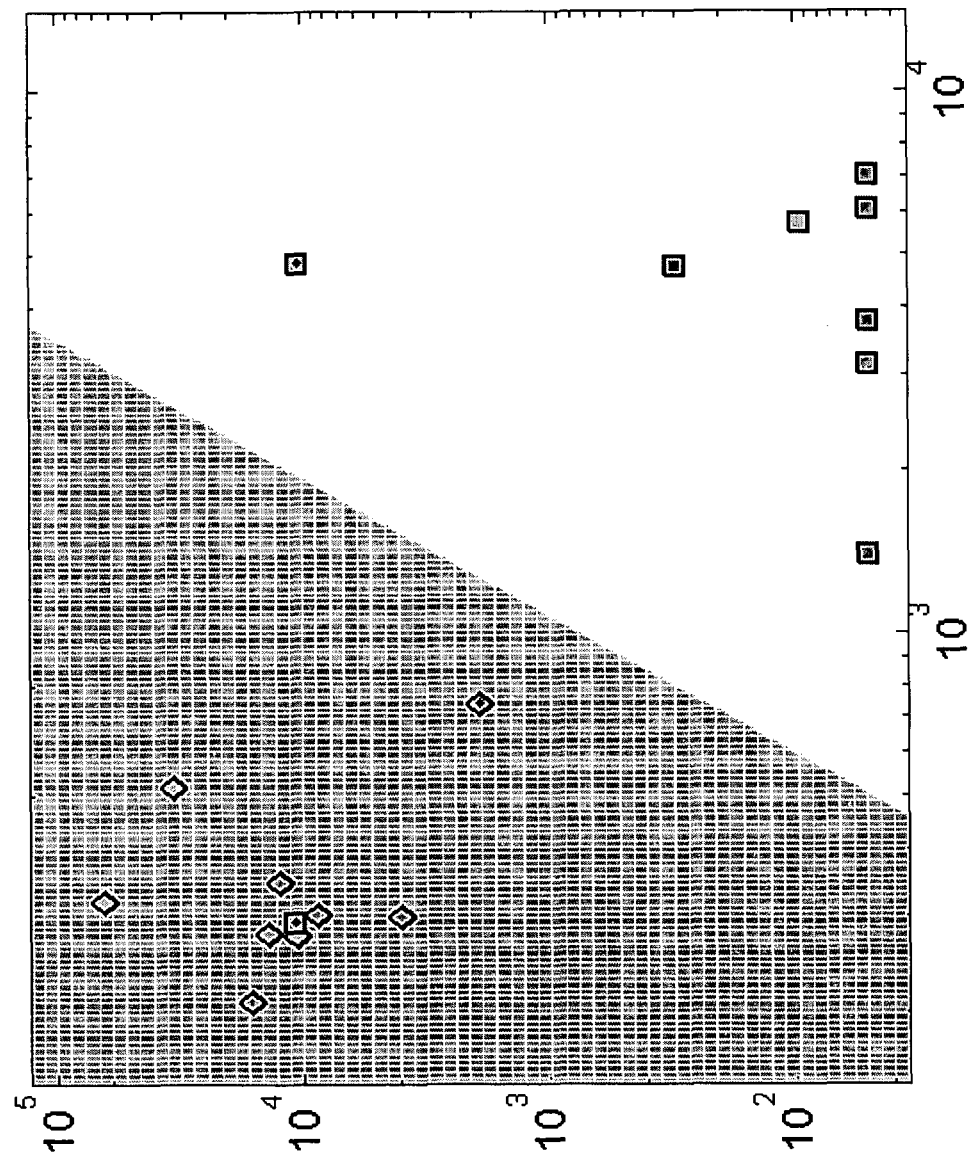

FIG. 11 demonstrates the classification of prostate primary tumors (diamond symbols) and prostate metastases (square symbols) using the expression levels of two microRNA biomarkers: hsa-miR-205 (SEQ ID NO: 1, Y-axis) and hsa-miR-210 (SEQ ID NO: 26, X-axis).

The diagonal line represents a possible binary classification such that patients below it may be treated aggressively.

Figure 12A:
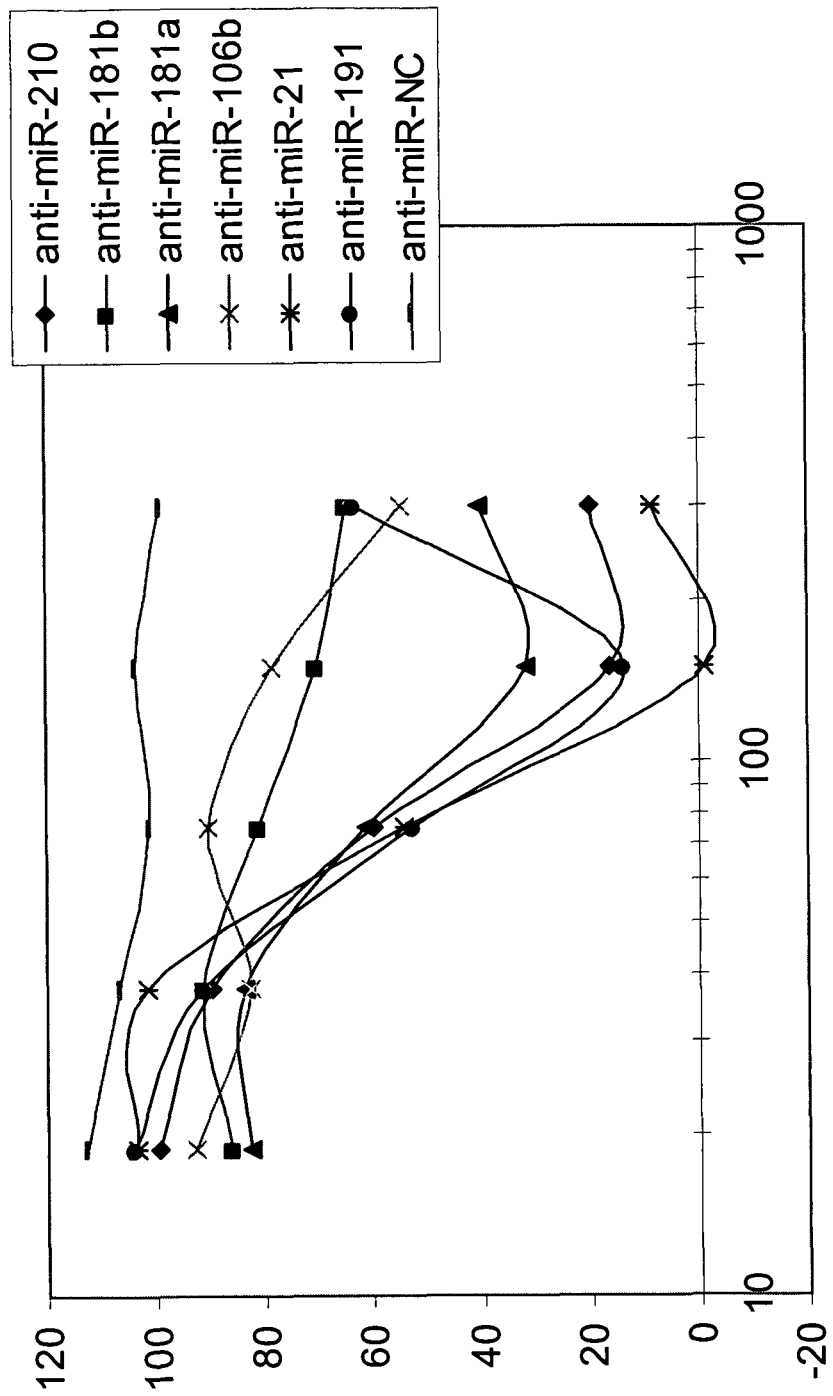

FIG. 12A demonstrates proliferation inhibition of PC-3 cells after treatment with specific anti-miRs as compared to anti-miR negative control (NC). Results were repeated in two independent studies.

Figure 12B:
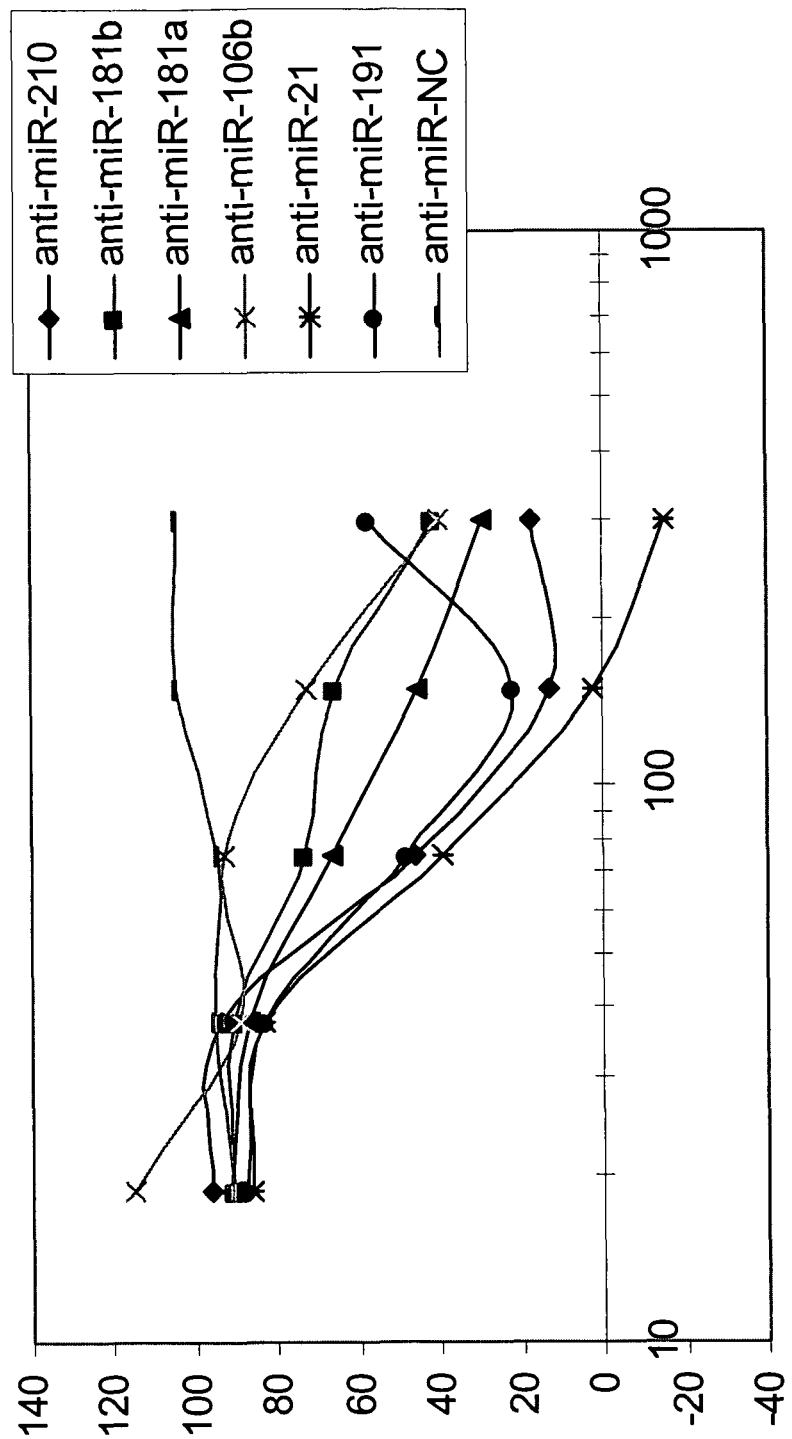

FIG. 12B demonstrates proliferation inhibition of DU-145 cells after treatment with specific anti-miRs as compared to anti-miR negative control (NC). Results were repeated in two independent studies.

DETAILED DESCRIPTION

According to some aspects of the present invention, miRNA expression can serve as a novel tool for determining the prognosis of patients with prostate cancer. More particularly, it may serve for the prediction of the risk for developing prostate metastases.

Methods and compositions are provided for determining the prognosis of prostate cancer. Methods and compositions for preventing or treating prostate cancer in a subject in need thereof are also provided.

Other aspects of the invention will become apparent to the skilled artisan by the following description of the invention.

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

1. Definitions

Administering

"Administering" means providing a pharmaceutical agent or composition to a subject, and includes, but is not limited to, administering by a medical professional and self-administering.

"Parenteral administration," means administration through injection or infusion. Parenteral administration includes, but is not limited to, subcutaneous administration, intravenous administration, or intramuscular administration.

"Subcutaneous administration" means administration just below the skin.

"Intravenous administration" means administration into a vein.

"Intratumoral administration" means administration within a tumor.

"Chemoembolization" means a procedure in which the blood supply to a tumor is blocked surgically or mechanically and chemotherapeutic agents are administered directly into the tumor.

Altered Expression

As used herein, the term "altered expression" encompasses over-expression, under-expression, and ectopic expression. According to some embodiments, the altered expression level is a change in a score based on a combination of expression levels of nucleic acid sequences or any combinations thereof.

Amelioration

Amelioration as used herein, refers to a lessening of severity of at least one indicator of a condition or disease. In certain embodiments, amelioration includes a delay or slowing in the progression of one or more indicators of a condition or disease. The severity of indicators may be determined by subjective or objective measures which are known to those skilled in the art.

Antisense

The term "antisense," as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated.

Biological Sample

"Biological sample" as used herein means a sample of biological tissue or fluid that comprises nucleic acids. Such samples include, but are not limited to, tissue or fluid isolated from subjects. Biological samples may also include sections of tissues such as biopsy and autopsy samples, FFPE samples, frozen sections taken for histological purposes, blood, plasma, serum, sputum, stool, tears, mucus, hair, and skin. Biological samples also include explants and primary and/or transformed cell cultures derived from animal or patient tissues.

Biological samples may also be blood, a blood fraction, urine, effusions, ascitic fluid, saliva, cerebrospinal fluid, cervical secretions, vaginal secretions, endometrial secretions, gastrointestinal secretions, bronchial secretions, sputum, cell line, tissue sample, cellular content of fine needle aspiration (FNA) or secretions from the breast. A biological sample may be provided by removing a sample of cells from an animal, but can also be accomplished by using previously isolated cells (e.g., isolated by another person, at another time, and/or for another purpose), or by performing the methods described herein in vivo. Archival tissues, such as those having treatment or outcome history, may also be used. Biological samples may also be stored in RNAlater® for analysis at a later date.

Cancer Prognosis

A forecast or prediction of the probable course or outcome of the cancer. As used herein, cancer prognosis includes the forecast or prediction of any one or more of the following: duration of survival of a patient susceptible to or diagnosed with a cancer, duration of recurrence-free survival, duration of progression-free survival of a patient susceptible to or diagnosed with a cancer, response to treatment in a group of patients susceptible to or diagnosed with a cancer, duration of response to treatment in a patient or a group of patients susceptible to or diagnosed with a cancer. As used herein, "prognostic for cancer" means providing a forecast or prediction of the probable course or outcome of the cancer. In some embodiments, "prognostic for cancer" comprises providing the forecast or prediction of (prognostic for) any one or more of the following: duration of survival of a patient susceptible to or diagnosed with a cancer, duration of recurrence-free survival, duration of progression-free survival of a patient susceptible to or diagnosed with a cancer, response to treatment in a group of patients susceptible to or diagnosed with a cancer, and duration of response to treatment in a patient or a group of patients susceptible to or diagnosed with a cancer.

Chemotherapeutic Agent

A drug used to treat a disease, especially cancer. In relation to cancer the drugs typically target rapidly dividing cells, such as cancer cells. Non-limiting examples of chemotherapeutic agents include cisplatin, carboplatin, camptothecins, doxorubicin, cyclophosphamide, paclitaxel, etoposide, vinblastine, Actinomycin D and cloposide.

Coadministration

The term "coadministration" or "combination therapy" is used to describe a therapy in which at least two active compounds (one of which is a compound according to the present invention) in effective amounts are used to treat prostate cancer, including metastatic prostate cancer as otherwise described herein at the same time. Although the term coadministration preferably includes the administration of two active compounds to the patient at the same time, it is not necessary that the compounds be administered-to-the patient at the same time, although effective amounts of the individual compounds will be present in the patient at the same time. Compounds according to the present invention may be administered with one or more compound including a chemotherapeutic agent such as dacarbazine (DTIC) and/or and immunotherapeufic agent such as IL-2 and/or α-interferon, among other compounds.

Complement

"Complement" or "complementary", as used herein to refer to a nucleic acid, may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules. In some embodiments, the complementary sequence has a reverse orientation (5'-3').

Detection

"Detection" means detecting the presence of a component in a sample. Detection also means detecting the absence of a component. Detection also means measuring the level of a component, either quantitatively or qualitatively.

Differential Expression

"Differential expression" may mean qualitative or quantitative differences in the temporal and/or cellular gene expression patterns within and among cells and tissue. Thus, a differentially expressed gene can qualitatively have its expression altered, including an activation or inactivation, in, e.g., normal versus disease tissue. Genes may be turned on or turned off in a particular state relative to another state, thus permitting comparison of two or more states. A qualitatively regulated gene will exhibit an expression pattern within a state or cell type that may be detectable by standard techniques. Some genes will be expressed in one state or cell type, but not in both. Alternatively, the difference in expression may be quantitative, e.g., in that expression is modulated, up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, and RNase protection.

Dose

"Dose" as used herein means a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

Dosage Unit

"Dosage unit" as used herein means a form in which a pharmaceutical agent is provided. In certain embodiments, a dosage unit is a vial containing lyophilized oligonucleotide. In certain embodiments, a dosage unit is a vial containing reconstituted oligonucleotide.

Effective

The term "effective" is used, to describe an amount of a composition, compound, or component, which produces an intended effect when used within the context of its use, which may be a diagnostic method, a therapeutic method, a method to monitor the progression of therapy or other method pursuant to the present invention. In the case of therapeutic methods, an effective amount for treating prostate cancer, including metastatic prostate cancer, is that amount which shrinks cancerous tissue (e.g., tumor), produces a remission, prevents further growth of the tumor and/or reduces the likelihood that the cancer in its early stages (in situ or invasive) does not progress further to metastatic prostate cancer.

Expression Profile

"Expression profile", as used herein, may mean a genomic expression profile, e.g., an expression profile of microRNAs. Profiles may be generated by any convenient means for determining a level of a nucleic acid sequence, e.g., quantitative hybridization of microRNA, labeled microRNA, amplified microRNA, cRNA, etc., quantitative PCR, ELISA for quantification, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more, including all of the listed nucleic acid sequences. The term "expression profile" may also mean measuring the abundance of the nucleic acid sequences in the measured samples.

Expression Ratio

"Expression ratio", as used herein, refers to relative expression levels of two or more nucleic acids as determined by detecting the relative expression levels of the corresponding nucleic acids in a biological sample.

Gene

"Gene", as used herein, may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Identity

"Identical" or "identity", as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

Inhibit

"Inhibit", as used herein, may mean prevent, suppress, repress, reduce or eliminate.

Label

"Label", as used herein, may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Logistic Regression

Logistic regression is part of a category of statistical models called generalized linear models. Logistic regression allows one to predict a discrete outcome, such as group membership, from a set of variables that may be continuous, discrete, dichotomous, or a mix of any of these. The dependent or response variable is dichotomous, for example, one of two possible types of cancer. Logistic regression models the natural log of the odds ratio, i.e., the ratio of the probability of belonging to the first group (P) over the probability of belonging to the second group (1-P), as a linear combination of the different expression levels (in log-space) and of other explaining variables. The logistic regression output can be used as a classifier by prescribing that a case or sample will be classified into the first type if P is greater than 0.5 or 50%. Alternatively, the calculated probability P can be used as a variable in other contexts such as a 1D or 2D threshold classifier.

1D/2D Threshold Classifier

"1D/2D threshold classifier", as used herein, may mean an algorithm for classifying a case or sample such as a cancer sample into one of two possible types such as two types of cancer or two types of prognosis (e.g., good and bad). For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A score may be calculated as a function (usually a continuous function) of the two variables; the decision is then reached by comparing the score to the predetermined threshold, similar to the 1D threshold classifier.

Mismatch

"Mismatch" means a nucleobase of a first nucleic acid that is not capable of pairing with a nucleobase at a corresponding position of a second nucleic acid.

Modified Oligonucleotide

"Modified oligonucleotide" as used herein means an oligonucleotide having one or more modifications relative to a naturally occurring terminus, sugar, nucleobase, and/or internucleoside linkage. According to one embodiment, the modified oligonucleotide is a miRNA comprising a modification (e.g. labeled). According to another embodiment, the modified oligonucleotide is complementary to a miRNA.

Nucleic Acid

"Nucleic acid" or "oligonucleotide" or "polynucleotide", as used herein, may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single-stranded or double-stranded, or may contain portions of both double-stranded and single-stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located, for example, at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e., ribonucleotides, containing a non-naturally occurring nucleobase instead of a naturally occurring nucleobase such as uridines or cytidines modified at the 5-position, e.g., 5-(2-amino)propyl uridine, 5-bromo uridine; adenosines and guanosines modified at the 8-position, e.g., 8-bromo guanosine; deaza nucleotides, e.g., 7-deaza-adenosine; O- and N-alkylated nucleotides, e.g., N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 2005; 438:685-689, Soutschek et al., Nature 2004; 432:173-178, and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Overall Survival Time

"Overall survival time" or "survival time", as used herein means the time period for which a subject survives after diagnosis of or treatment for a disease. In certain embodiments, the disease is prostate cancer.

Partially Complementary

As used herein, "partially complementary" refers to less than 100% complementary base pairing between nucleotides or nucleotide analogs of nucleic acid molecules. In some embodiments the base-paring spans only a specific section of the partially complementary nucleic acid molecules.

Pharmaceutical Agent

Pharmaceutical agent as used herein means a substance that provides a therapeutic effect when administered to a subject. "Pharmaceutical composition" means a mixture of substances suitable for administering to an individual that includes a pharmaceutical agent. For example, a pharmaceutical composition may comprise a modified oligonucleotide and a sterile aqueous solution. "Active pharmaceutical ingredient" means the substance in a pharmaceutical composition that provides a desired effect.

Prevention

Prevention as used herein means delaying or forestalling the onset or development or progression of a condition or disease for a period of time, including weeks, months, or years.

Progression-Free Survival

"Progression-free survival" means the time period for which a subject having a disease survives, without the disease getting worse. In certain embodiments, progression-free survival is assessed by staging or scoring the disease. In certain embodiments, progression-free survival of a subject having cancer is assessed by evaluating tumor size, tumor number, and/or metastasis.

Probe

"Probe", as used herein, may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence, depending upon the stringency of the hybridization conditions. There may be any number of base pair mismatches which will interfere with hybridization between the target sequence and the single-stranded nucleic acids described herein. However, if the number of mutations is so great that no hybridization can occur under even the least stringent of hybridization conditions, the sequence is not a complementary target sequence. A probe may be single-stranded or partially single- and partially double-stranded. The strandedness of the probe is dictated by the structure, composition, and properties of the target sequence. Probes may be directly labeled or indirectly labeled such as with biotin to which a streptavidin complex may later bind.

Reduced Tumorigenicity

"Reduced tumorigenicity" as used herein refers to the conversion of hyperproliferative (e.g., neoplastic) cells to a less proliferative state. In the case of tumor cells, "reduced tumorigenicity" is intended to mean tumor cells that have become less tumorigenic or non-tumorigenic or non-tumor cells whose ability to convert into tumor cells is reduced or eliminated. Cells with reduced tumorigenicity either form no tumors in vivo or have an extended lag time of weeks to months before the appearance of in vivo tumor growth. Cells with reduced tumorigenicity may also result in slower growing three dimensional tumor mass compared to the same type of cells having fully inactivated or non-functional tumor suppressor gene growing in the same physiological milieu (e.g., tissue, organism age, organism sex, time in menstrual cycle, etc.).

Reference Value

As used herein, the term "reference value" means a value that statistically correlates to a particular outcome when compared to an assay result. In preferred embodiments the reference value is determined from statistical analysis of studies that compare microRNA expression with known clinical outcomes. The reference value may be a threshold score value or a cutoff score value. Typically, a reference value will be a threshold above which one outcome is more probable and below which an alternative outcome is more probable.

Sensitivity

"Sensitivity", as used herein, may mean a statistical measure of how well a binary classification test correctly identifies a condition, for example, how frequently it correctly classifies a cancer into the correct type out of two possible types. The sensitivity for class A is the proportion of cases that are determined to belong to class "A" by the test out of the cases that are in class "A", as determined by some absolute or gold standard.

Side Effect

Side effect as used herein means a physiological response attributable to a treatment other than desired effects.

Specificity

"Specificity", as used herein, may mean a statistical measure of how well a binary classification test correctly identifies a condition, for example, how frequently it correctly classifies a cancer into the correct type out of two possible types. The specificity for class A is the proportion of cases that are determined to belong to class "not A" by the test out of the cases that are in class "not A", as determined by some absolute or gold standard.

Stringent Hybridization Conditions

"Stringent hybridization conditions", as used herein, may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary", as used herein, may mean that a first sequence is at least 60%-99% identical to the complement of a second sequence over a region of 8-50 or more nucleotides, or that the two sequences hybridize under stringent hybridization conditions.

Substantially Identical

"Substantially identical", as used herein, may mean that a first and second sequence are at least 60%-99% identical over a region of 8-50 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Therapeutically Effective Amount

"Therapeutically effective amount" or "therapeutically efficient" used herein as to a drug dosage, refer to dosage that provides the specific pharmacological response for which the drug is administered in a significant number of subjects in need of such treatment. The "therapeutically effective amount" may vary according, for example, the physical condition of the patient, the age of the patient and the severity of the disease.

Threshold Expression Level

As used herein, the phrase "threshold expression level" refers to a criterion expression profile to which measured values are compared in order to determine the prognosis of a subject with prostate cancer. The reference expression profile may be based on the expression of the nucleic acids, or may be based on a combined metric score thereof.

Tissue Sample

As used herein, a tissue sample is tissue obtained from a tissue biopsy using methods well known to those of ordinary skill in the related medical arts. The phrase "suspected of being cancerous", as used herein, means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Treat

"Treat" or "treating", as used herein when referring to protection of a subject from a condition, may mean preventing, suppressing, repressing, or eliminating the condition. Preventing the condition involves administering a composition described herein to a subject prior to onset of the condition. Suppressing the condition involves administering the composition to a subject after induction of the condition but before its clinical appearance. Repressing the condition involves administering the composition to a subject after clinical appearance of the condition such that the condition is reduced or prevented from worsening. Elimination of the condition involves administering the composition to a subject after clinical appearance of the condition such that the subject no longer suffers from the condition.

Tumor

"Tumor", as used herein, refers to all neoplastic cell growth and proliferation, whether malignant or benign, and all pre-cancerous and cancerous cells and tissues.

Unit Dosage Form

"Unit dosage form" used herein may refer to a physically discrete unit suitable as a unitary dosage for a human or animal subject. Each unit may contain a predetermined quantity of a composition described herein, calculated in an amount sufficient to produce a desired effect in association with a pharmaceutically acceptable diluent, carrier or vehicle. The specifications for a unit dosage form may depend on the particular composition employed and the effect to be achieved, and the pharmacodynamics associated with the composition in the host.

Variant

"Variant", as used herein to refer to a nucleic acid, may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

Vector

"Vector", as used herein, may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. Prostate Cancer, its Stages and Treatment

Prostate cancer is a malignancy occurring in the male prostate gland. The term "cancer" or "neoplasm" generally means a malignant disease and is characterized by an uncontrolled growth of tumor or cancer cells. Tumors may spread locally as a primary tumor mass or spread to distant parts of the body, i.e., metastasize.

According to the National Cancer Institute (U.S. National Institutes of Health, 2008) the following four stages (A to D) are used for prostate cancer:

Stage A, microscopic cancer within prostate, is further subdivided into stages A1 and A2. Sub-stage A1 is a well-differentiated cancer confined to one site within the prostate. Treatment is generally observation, radical prostatectomy, or radiation. Sub-stage A2 is a moderately to poorly differentiated cancer at multiple sites within the prostate. Treatment is radical prostatectomy or radiation. Stage B, palpable lump within the prostate, is also further subdivided into sub-stages B1 and B2. In sub-stage B1, the cancer forms a small nodule in one lobe of the prostate. In sub-stage B2, the cancer forms large or multiple nodules, or occurs in both lobes of the prostate. Treatment for sub-stages B1 and B2 is either radical prostatectomy or radiation. Stage C is a large cancer mass involving most or all of the prostate and is also further subdivided into two sub-stages. In sub-stage C1, the cancer forms a continuous mass that may have extended beyond the prostate. In sub-stage C2, the cancer forms a continuous mass that invades the surrounding tissue. Treatment for both these sub-stages is radiation with or without drags to address the cancer. The fourth stage, Stage D is metastatic cancer and is also subdivided into two sub-stages. In sub-stage D1, the cancer appears in the lymph nodes of the pelvis. In sub-stage D2, the cancer involves tissues beyond lymph nodes. Treatment for both of these sub-stages is systemic drugs to address the cancer as well as pain.

However, current prostate cancer staging methods are limited. As many as 50% of prostate cancers initially staged as A2, B, or C are actually stage D, metastatic. Discovery of metastasis is significant because patients with metastatic cancers have a poorer prognosis and require significantly different therapy than those with localized cancers. The five year survival rates for patients with localized and metastatic prostate cancers are 93% and 29%, respectively.

Surgery to remove the tumor is the primary treatment of all stages of prostate. (The surgery may be local excision or lymphadenectomy, in which the lymph nodes are also removed.) Chemotherapy (regional or systemic), radiation therapy (external or internal) and immunotherapy may further be provided.

3. Micrornas and Their Processing

A gene coding for a miRNA may be transcribed, leading to production of an miRNA precursor known as the pri-miRNA. The pri-miRNA may be part of a polycistronic RNA comprising multiple pri-miRNAs. The pri-miRNA may form a hairpin with a stem and loop. The stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 30-200 nt precursor known as the pre-miRNA. Drosha may cleave the pri-miRNA with a staggered cut typical of Rnase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an Rnase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the miRNA, especially by nucleotides 2-8 of the miRNA. Only one case has been reported in animals where the interaction between the miRNA and its target was along the entire length of the miRNA. This was shown for miR-196 and Hox B8 and it was further shown that miR-196 mediates the cleavage of the Hox B8 mRNA (Yekta et al., Science 2004; 304:594-596). Otherwise, such interactions are known only in plants (Bartel & Bartel, Plant Physiol 2003; 132:709-717).

A number of studies have looked at the base-pairing requirement between miRNA and its mRNA target for achieving efficient inhibition of translation (reviewed by Bartel, Cell 2004; 116:281-297). In mammalian cells, the first 8 nucleotides of the miRNA may be important (Doench & Sharp, Genes Dev 2004; 18:504-511). However, other parts of the microRNA may also participate in mRNA binding. Moreover, sufficient base pairing at the 3' can compensate for insufficient pairing at the 5' (Brennecke et al., PloS Biol 2005; 3:e85). Computation studies, in which miRNA binding on whole genomes is analyzed, have suggested a specific role for bases 2-7 at the 5' of the miRNA in target binding, but the role of the first nucleotide, found usually to be "A", was also recognized (Lewis et al., Cell 2005; 120:15-20). Similarly, nucleotides 1-7 or 2-8 were used by Krek et al., Nat Genet. 2005; 37:495-500) to identify and validate targets The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to down-regulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

4. Nucleic Acids

Nucleic acids are provided herein. The nucleic acid may comprise the sequence of SEQ ID NOS: 1-101 presented in Tables 1, 2 and 3, or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single-strand molecule and hybridized to a substantially complementary nucleic acid to form a duplex. The nucleic acid may be introduced to a cell, tissue or organ in a single- or double-stranded form or may be capable of being expressed by a synthetic gene using methods well known to those skilled in the art, including as described in U.S. Pat. No. 6,506,559, which is incorporated by reference.

a. Nucleic Acid Complex

The nucleic acid may further comprise one or more of the following: a peptide, a protein, a RNA-DNA hybrid, an antibody, an antibody fragment, a Fab fragment, and an aptamer. The nucleic acid may also comprise a protamine-antibody fusion protein as described in Song et al. (Nature Biotechnology 2005; 23:709-17) and Rossi (Nature Biotechnology 2005; 23:682-4), the contents of which are incorporated herein by reference. The protamine-fusion protein may comprise the abundant and highly basic cellular protein protamine. The protamine may readily interact with the nucleic acid. The protamine may comprise the entire 51-amino acid protamine peptide or a fragment thereof. The protamine may be covalently attached to another protein, which may be a Fab. The Fab may bind to a receptor expressed on a cell surface.

b. Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-91 or variants thereof.

The pri-miRNA may form a hairpin structure. The hairpin may comprise first and second nucleic acid sequence that are substantially complementary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole, as calculated by the Vienna algorithm, with default parameters, as described in Hofacker et al. (Monatshefte f. Chemie 1994; 125:167-188), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

c. Pre-miRNA

The nucleic acid may also comprise a sequence of a pre-miRNA or a variant thereof. The pre-miRNA sequence may comprise from 45-200; 60-80 or 60-70 nucleotides. The sequence of the pre-miRNA may comprise a miRNA and a miRNA*, as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-91 or variants thereof.

d. MiRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-36, 75, 77, 79, 81, 83, 85, 87 and 89 or variants thereof.

e. Anti-miRNA

The nucleic acid may also comprise a sequence of an anti-miRNA that is capable of blocking the activity of a miRNA or miRNA*, such as by binding to the pri-miRNA, pre-miRNA, miRNA or miRNA* (e.g., antisense or RNA silencing), or by binding to the target binding site. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the anti-miRNA may comprise (a) at least 5 nucleotides that are substantially identical or complementary to the 5' of a miRNA and at least 5-12 nucleotides that are substantially complementary to the flanking regions of the target site from the 5' end of the miRNA, or (b) at least 5-12 nucleotides that are substantially identical or complementary to the 3' of a miRNA and at least 5 nucleotides that are substantially complementary to the flanking region of the target site from the 3' end of the miRNA. The sequence of the anti-miRNA may comprise the complement of SEQ ID NOS: 1-36, 75, 77, 79, 81, 83, 85, 87 and 89 or variants thereof

5. Probes

A probe comprising a nucleic acid described herein is also provided. Probes may be used for screening and diagnostic methods. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

6. Biochip

A biochip is also provided. The biochip may comprise a solid substrate comprising an attached probe or plurality of probes described herein. The probes may be capable of hybridizing to a target sequence under stringent hybridization conditions. The probes may be attached at a spatially defined address on the substrate. More than one probe per target sequence may be used, with either overlapping probes or probes to different sections of a particular target sequence. The probes may be capable of hybridizing to target sequences associated with a single disorder, as appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes, and Is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as a flexible foam, including closed-cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

7. Diagnosis

A method of diagnosis is provided. The method comprises detecting a differential expression level of prostate cancer-associated nucleic acid in a biological sample. The sample may be derived from a subject. Diagnosis of a disease state in a patient may allow for prognosis and selection of therapeutic strategy. Further, the developmental stage of cells may be determined by determining temporarily expressed prostate cancer-associated nucleic acids.

In situ hybridization of labeled probes to tissue sections may be performed. When comparing the fingerprints between an individual and a standard, the skilled artisan can make a diagnosis, a prognosis, or a prediction based on the findings. It is further understood that the nucleic acids which indicate the diagnosis may differ from those which indicate the prognosis and molecular profiling of the condition of the cells may lead to distinctions between responsive or refractory conditions or may be predictive, of outcomes.

8. Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein.

For example, the kit may be a kit for the amplification, detection, identification or quantification of a target nucleic acid sequence. The kit may comprise a poly(T) primer, a forward primer, a reverse primer, and a probe.

9. Compositions

A pharmaceutical composition is also provided. The composition may comprise a nucleic acid described herein and optionally a pharmaceutically acceptable carrier. The composition may encompass modified oligonucleotides that are identical, substantially identical, substantially complementary or complementary to any nucleobase sequence version of the miRNAs described herein or a precursor thereof.

In certain embodiments, a nucleobase sequence of a modified oligonucleotide is fully identical or complementary to a miRNA nucleobase sequence listed herein, or a precursor thereof. In certain embodiments, a modified oligonucleotide has a nucleobase sequence having one mismatch with respect to the nucleobase sequence of the mature miRNA, or a precursor thereof. In certain embodiments, a modified oligonucleotide has a nucleobase sequence having two mismatches with respect to the nucleobase sequence of the miRNA, or a precursor thereof. In certain such embodiments, a modified oligonucleotide has a nucleobase sequence having no more than two mismatches with respect to the nucleobase sequence of the mature miRNA, or a precursor thereof. In certain such embodiments, the mismatched nucleobases are contiguous. In certain such embodiments, the mismatched nucleobases are not contiguous.

In certain embodiments, a modified oligonucleotide consists of a number of linked nucleosides that is equal to the length of the mature miRNA.

In certain embodiments, the number of linked nucleosides of a modified oligonucleotide is less than the length of the mature miRNA. In certain such embodiments, the number of linked nucleosides of a modified oligonucleotide is one less than the length of the mature miRNA. In certain such embodiments, a modified oligonucleotide has one less nucleoside at the 5' terminus. In certain such embodiments, a modified oligonucleotide has one less nucleoside at the 3' terminus. In certain such embodiments, a modified oligonucleotide has two fewer nucleosides at the 5' terminus. In certain such embodiments, a modified oligonucleotide has two fewer nucleosides at the 3' terminus. A modified oligonucleotide having a number of linked nucleosides that is less than the length of the miRNA, wherein each nucleobase of a modified oligonucleotide is complementary to each nucleobase at a corresponding position in: miRNA, is considered to be a modified oligonucleotide having a nucleobase sequence that is fully complementary to a portion of a miRNA sequence.

In certain embodiments, a modified oligonucleotide consists of 15 to 30 linked nucleosides. In certain embodiments, a modified oligonucleotide consists of 19, to 24 linked nucleosides. In certain embodiments, a modified oligonucleotide consists of 21 to 24 linked nucleosides. In certain embodiments, a modified oligonucleotide consists of 15 linked nucleosides. In certain embodiments, a modified oligonucleotide consists of 16 linked nucleosides. In certain embodiments, a modified oligonucleotide consists of 17 linked nucleosides. In certain embodiments, a modified oligonucleotide consists of 18 linked nucleosides. In certain embodiments, a modified oligonucleotide consists of 19 linked nucleosides. In certain embodiments, a modified oligonucleotide consists of 20 linked nucleosides. In certain embodiments, a modified oligonucleotide consists of 21 linked nucleosides. In certain embodiments, a modified oligonucleotide consists of 22 linked nucleosides. In certain embodiments, a modified oligonucleotide consists of 23 linked nucleosides. In certain embodiments, a modified oligonucleotide consists of 24 linked nucleosides. In certain embodiments, a modified oligonucleotide consists of 25 linked nucleosides. In certain embodiments, a modified oligonucleotide consists of 26 linked nucleosides. In certain embodiments, a modified oligonucleotide consists of 27 linked nucleosides. In certain embodiments, a modified oligonucleotide consists of 28 linked nucleosides. In certain embodiments, a modified oligonucleotide consists of 29 linked nucleosides. In certain embodiments, a modified oligonucleotide consists of 30 linked nucleosides.

Modified oligonucleotides of the present invention may comprise one or more modifications to a nucleobase, sugar, and/or internucleoside linkage. A modified nucleobase, sugar, and/or internucleoside linkage may be selected over an unmodified form because of desirable properties such as, for example, enhanced cellular uptake, enhanced affinity for other oligonucleotides or nucleic acid targets and increased stability in the presence of nucleases.

In certain embodiments, a modified oligonucleotide of the present invention comprises one or more modified nucleosides. In certain such embodiments, a modified nucleoside is a stabilizing nucleoside. An example of a stabilizing nucleoside is a sugar-modified nucleoside.

In certain embodiments, a modified nucleoside is a sugar-modified nucleoside. In certain such embodiments, the sugar-modified nucleosides can further comprise a natural or modified heterocyclic base moiety and/or a natural or modified internucleoside linkage and may include further modifications independent from the sugar modification. In certain embodiments, a sugar modified nucleoside is a 2'-modified nucleoside, wherein the sugar ring is modified at the 2' carbon from natural ribose or 2'-deoxy-ribose. In certain embodiments, 2'-O-methyl group is present in the sugar residue.

The modified oligonucleotides designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

It will be appreciated that an oligonucleotide comprising an RNA molecule can be also generated using an expression vector as is further described hereinbelow.

The compositions may be used for therapeutic applications. The pharmaceutical composition may be administered by known methods, including wherein a nucleic acid is introduced into a desired target cell in vitro or in vivo.

Methods for the delivery of nucleic acid molecules are described in Akhtar et al., (Trends Cell Bio. 2, 139, 1992). WO 94/02595 describes general methods for delivery of RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, Neuroscience, 76, 1153-1158). Other approaches include the use of various transport and carrier systems, for example, through the use of conjugates and biodegradable polymers. More detailed descriptions of nucleic acid delivery and administration are provided for example in WO93/23569, WO99/05094, and WO99/04819.

The nucleic acids can be introduced into tissues or host cells by any number of routes, including viral infection, microinjection, or fusion of vesicles. Jet injection may also be used for intra-muscular administration, as described by Furth et al. (Anal Biochem 115 205:365-368, 1992). The nucleic acids can be coated onto gold microparticles, and delivered intradermally by a particle bombardment device, or "gene gun" as described in the literature (see, for example, Tang et al. Nature 356:152-154, 1992), where gold microprojectiles are coated with the DNA, then bombarded into skin cells.

The compositions of the present invention can be formulated into pharmaceutical compositions by combination with appropriate, pharmaceutically acceptable carriers or diluents, and can be formulated into preparations in solid, semi-solid, liquid or gaseous forms, such as tablets, capsules, powders, granules, ointments, solutions, suppositories, injections, inhalants and aerosols. As such, administration of the agents can be achieved in various ways, including oral, buccal, rectal, parenteral, intraperitoneal, intradermal, transdermal, intracheal, etc.

In certain embodiments, a pharmaceutical composition of the present invention is administered in the form of a dosage unit (e.g., tablet, capsule, bolus, etc.). In certain embodiments, such pharmaceutical compositions comprise a modified oligonucleotide in a dose selected from 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, and 800 mg. In certain such embodiments, a pharmaceutical composition of the present invention comprises a dose of modified oligonucleotide selected from 25 mg, 50 mg, 75 mg, 100 mg, 150 mg, 200 mg, 250 mg, 300 mg, 350 mg, 400 mg, 500 mg, 600 mg, 700 mg, and 800 mg.

In certain embodiments, a pharmaceutical agent is sterile lyophilized modified oligonucleotide that is reconstituted with a suitable diluent, e.g., sterile water for injection or sterile saline for injection. The reconstituted product is administered as a subcutaneous injection or as an intravenous infusion after dilution into saline. The lyophilized drug product consists of a modified oligonucleotide which has been prepared in water for injection, or in saline for injection, adjusted to pH 7.0-9.0 with acid or base during preparation, and then lyophilized. The lyophilized modified oligonucleotide may be 25-800 mg of a modified oligonucleotide. It is understood that this encompasses 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of modified lyophilized oligonucleotide.

In certain embodiments, the compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms, of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the oligonucleotide (s) of the formulation.

In certain embodiments, pharmaceutical compositions of the present invention comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition of the present invention is prepared using known techniques, including, but not limited to mixing, dissolving, granulating, dragee-making, levigating, emulsifying, encapsulating, entrapping or tabletting processes.

In certain embodiments, a pharmaceutical composition of the present invention is a liquid (e.g., a suspension, elixir and/or solution). In certain of such embodiments, a liquid pharmaceutical composition is prepared using ingredients known in the art, including, but not limited to, water, glycols, oils, alcohols, flavoring agents, preservatives, and coloring agents.

In certain embodiments, a pharmaceutical composition of the present invention is a solid (e.g., a powder, tablet, and/or capsule). In certain of such embodiments, a solid pharmaceutical composition comprising one or more oligonucleotides is prepared using ingredients known in the art, including, but not limited to, starches, sugars, diluents, granulating agents, lubricants, binders, and disintegrating agents.

In certain embodiments, a pharmaceutical composition of the present invention is formulated as a depot preparation. Certain such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition of the present invention comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition of the present invention comprises a sustained-release system. A non-limiting example of such a sustained-release system is a semi-permeable matrix of solid hydrophobic polymers. In certain embodiments, sustained-release systems may, depending on their chemical nature, release pharmaceutical agents over a period of hours, days, weeks or months.

In certain embodiments, a pharmaceutical composition of the present invention is prepared for oral administration. In certain of such embodiments, a pharmaceutical composition is formulated by combining one or more compounds comprising modified oligonucleotides with one or more pharmaceutically acceptable carriers. Certain of such carriers enable pharmaceutical compositions to be formulated as tablets, pills, dragees, capsules, liquids, gels, syrups, slurries, suspensions and the like, for oral ingestion by a subject. In certain embodiments, pharmaceutical compositions for oral use are obtained by mixing oligonucleotide and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more pharmaceutical agents of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more pharmaceutical agents of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a pharmaceutical agent of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, and lanolin and water in oil emulsions. Exemplary suitable cream bases include, but are not limited to, cold cream and hydrophilic ointment.

In certain embodiments, a pharmaceutical composition of the present invention comprises a modified oligonucleotide in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, one or more modified oligonucleotides of the present invention are formulated as a prodrug. In certain embodiments, upon in vivo administration, a prodrug is chemically converted to the biologically, pharmaceutically or therapeutically more active form of a modified oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, a prodrug is produced by modifying a pharmaceutically active compound such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

10. Therapeutic

A method for treating prostate cancer in vivo or ex vivo is also provided. Furthermore, existing miRNA molecules may be used as starting materials for the manufacture of sequence-modified miRNA molecules. Further, miRNA molecules may be modified, in order that they are processed and then generated as double-stranded siRNAs which are again directed against therapeutically relevant targets.

As previously discussed the methods, compositions and articles of manufacture of the present invention are particularly useful in the treatment of cancer, neurodegenerative disorder and infectious disease.

The compositions of the present invention may be combined with a chemotherapeutic agent, a combination of chemotherapeutic agents and/or radiotherapy.

Cancer treatments often comprise more than one therapy. As such, in certain embodiments the present invention provides methods for treating cancer comprising administering to a subject in need thereof the composition of the present invention, and further comprising administering at least one additional therapy.

In certain embodiments, an additional therapy may also be designed to treat cancer. An additional therapy may be a chemotherapeutic agent. Suitable chemotherapeutic agents include 5-fluorouracil, gemcitabine, doxorubicine, mitomycin c, sorafenib, etoposide, carboplatin, epirubicin, irinotecan and oxaliplatin. An additional therapy may be surgical resection of tumor(s), or chemoembolization.

Having now generally described the invention, the same will be more readily understood through reference to the following examples, which are provided by way of illustration and are not intended to be limiting of the present invention:

EXAMPLES

Example 1

Materials and Methods

Biological Samples:

The first experiment was based on nine brain metastasis of prostate cancer, origin specimens and nine primary prostate cancer specimens.

The second experiment included nine metastasis of prostate cancer origin specimens (4 brain, 1 lung, 1 lymph node, 2 spine and 1 spinal cord) and 18 primary prostate cancer specimens.

Total RNA enriched in microRNA was isolated from the formalin-fixed, paraffin-embedded (FFPE) specimens, and all RNAs extracted were hybridized onto microarrays according to the RNA extraction and microRNA array platform protocols described below.

RNA Extraction:

For FFPE samples, total RNA was isolated from five to ten 10-μm-thick tissue sections using the microRNA extraction protocol developed at Rosetta Genomics. Briefly, the sample is incubated repeatedly in Xylene at 57° C. to remove paraffin excess, followed by repeated ethanol washes. Proteins are degraded by proteinase K solution at 45° C. for a few hours. The RNA is extracted with acid phenol:chloroform, followed by ethanol precipitation and DNAse digestion. Total RNA quantity and quality is checked by spectrophotometer (Nanodrop ND-1000).

microRNA Array Platform:

Custom microarrays were produced by printing DNA oligonucleotide probes representing 911 human microRNAs. Each probe, printed in triplicate, carries a linker up to 22 nt long at the 3' end of the complement sequence of the microRNA, in addition to an amine group used to couple the probes to coated glass slides. 20 μM of each probe were dissolved in 2×SSC+0.0035% SDS and spotted in triplicate on Schott Nexterion® Slide E-coated microarray slides using a Genomic Solutions® BioRobotics MicroGrid II, according the MicroGrid manufacturer's directions. Fifty-four negative control probes were designed using the sense sequences of different microRNAs. Two groups of positive control probes were designed to hybridize to a miRNAarray: (i) synthetic small RNA were spiked to the RNA before labeling to verify the labeling efficiency and (ii) probes for abundant small RNA (e.g., small nuclear RNAs (U43, U49, U24, Z30, U6, U48, U44), 5.8s and 5s ribosomal RNA) were spotted on the array to verify RNA quality. The slides were blocked in a solution containing 50 mM ethanolamine, 1 M Tris (pH 9.0) and 0.1% SDS for 20 min at 50° C., then thoroughly rinsed with water and spun dry.

Agilent custom microarrays (Biochips) were manufactured by Agilent Technologies. In situ synthesizing DNA oligonucleotide probes to 982 microRNAs were printed in triplicate. Each probe comprised an antisense sequence of the relevant sequence, followed by a tail sequence GCAATGCTAGCTATTGCTTGCTATTAAAAA (SEQ ID NO: 101), and trimmed to the length of 45 nucleotides. Seventeen negative control probes were designed using the sense sequences of different microRNAs. Two groups of positive control probes were designed to hybridize to the array: (i) synthetic small RNA that were spiked to the sample RNA before labeling to verify the labeling efficiency, and (ii) probes for abundant small nuclear RNAs were spotted on the array to verify RNA quality.

Cy-Dye Labeling of microRNA for microRNA Array:

3.5 μg of total RNA were labeled by ligation (Thomson et al., Nature Methods 2004; 1:47-53) of an RNA-linker, p-rCrU-Cy/dye (Eurogentec S. A.; Cy3 or Cy5), to the 3' end with Cy3 or Cy5. The labeling reaction contained total RNA, spikes (0.1-20 fmoles), 300 ng RNA-linker-dye; 15% DMSO, 1× ligase buffer and 20 units of T4 RNA ligase (NEB) and proceeded at 4° C. for 1 h, followed by 1 h at 37° C. The labeled RNA was mixed with 3× hybridization buffer (Ambion), heated to 95° C. for 3 min and then added on top of the microarray. Slides were hybridized 12-16 h in 42° C., followed by two washes in room temperature with 1×SSC and 0.2% SDS and a final wash with 0.1×SSC.

Arrays were scanned using an Agilent Microarray Scanner Bundle G2565BA (resolution of 10 μm at 100% power). Array images were analyzed using SpotReader software (Niles Scientific).

For Agilent custom microarrays, a total of 1 μg of total RNA was labeled by ligation of an RNA-linker, p-rCrU-Cy/dye (Eurogentec S. A.; Cy3 or Cy5), to the 3' end. Synthetic small RNA was spiked into the RNA before labeling to verify the labeling efficiency. Slides were incubated with the labeled RNA for 12-16 h at 54-55° C. and then washed according to Agilent GE washes. Arrays were scanned using Agilent DNA Microarray Scanner Bundle (Agilent Technologies, Santa Clara, Calif.) at a resolution of 5 micrometer, dual pass at 100% and 10% PMT power. Array images were analyzed using Agilent Feature Extraction software. Array images were analyzed using the Feature Extraction software (FE) 9.5.1 (Agilent, Santa Clara, Calif.).

Array Data Normalization:

The initial data set consisted of signals measured for multiple probes for every sample. For the analysis, signals were used only for probes that were designed to measure the expression levels of known or validated human microRNAs.

Triplicate spots were combined into one signal by taking the logarithmic mean of the reliable spots. All data was log-transformed and the analysis was performed in log-space. A reference data vector for normalization, R, was calculated by taking the median expression level for each probe across all samples.

For each sample k with data vector $S^k$, a 2nd degree polynomial $F^k$ was found so as to provide the best fit between the sample data and the reference data, such that $R \approx F^k(S^k)$. Remote data points ("outliers") were not used for fitting the polynomials F. For each probe in the sample (element $S_i^k$ in the vector $S^k$), the normalized value (in log-space) $M_i^k$ is calculated from the initial value $S_i^k$ by transforming it with the polynomial function $F^k$, so that $M_i^k = F^k(S_i^k)$. Statistical analysis is performed in log-space. For presentation and calculation of fold-change, data is translated back to linear-space by taking the exponent.

Data Analysis:

In order to identify microRNA signatures that can be used to predict prostate cancer progression, the expression levels of microRNA in samples from prostate primary tumors and metastatic tumors from prostate origin were compared (see Tables 1-2). P-values were calculated using a two-sided unpaired t-test on the log-transformed normalized signal. Fold-changes were calculated by the change in the median values of the normalized fluorescence signal for each microRNA. For each microRNA, the ability to separate the two groups by the Receiver operating characteristic (ROC) curve was characterized and the calculated area under the ROC curve was marked as AUC. An optimal classifier which reaches sensitivity and specificity of 100% has AUC=1; a random classifier has AUC=0.5. To test the ability of microRNA expression levels to differentiate the two groups, an automatic classifier was constructed that chooses the microRNAs with the highest AUC, and classifies using logistic regression classifier in the space of these microRNAs (in log-space). This classifier reached sensitivity of 100% and specificity of 100%. Similar results can be obtained using any other classifier such as simple SVM (linear kernel), LDA classifiers or KNN.

Proliferation Assay Using Anti-miRs in Prostate Metastatic Cell Lines:

PC3 and DU145, prostate metastatic cell lines were purchased from NCI-NIH. Anti-miR molecules were purchased from IDT, and harboured 2-OMe modifications with phosphorothioate backbone onto the reverse compliment sequence of the relevant miR.

Cells were seeded in 96 well plates at a density of 2,500 cells per well. 24 h after seeding, cells were transfected with anti-miR. Transfection of cells with anti-miRs was done using Oligofectamine (Invitrogen, Cat#12252011), according to manufacturer instructions. In short cells were exposed to anti-miR and transfection reagent complex in OptiMEM for 4 h at a concentration range of 20-300 nM, in duplicates. After that transfection media was removed and full supplemented media was applied.

72 h after transfection, cells were tested for proliferation using cell Proliferation Assay kit-cellTiter 96 AQueous One solution (Promega, Cat#G3581), according to manufacture instructions. Absorbance was measured at 490 nm, using ELx808 ultra microplate reader (BIO-TEK instruments, INC). Absorbance was blanked using medium and calculated as % of untreated cells. At day of transfection another plate with non-treated cells were also tested for proliferation. This result was subtracted from the 72 h read, so proliferation is calculated from the time of transfection.

Example 2

Figure 1:
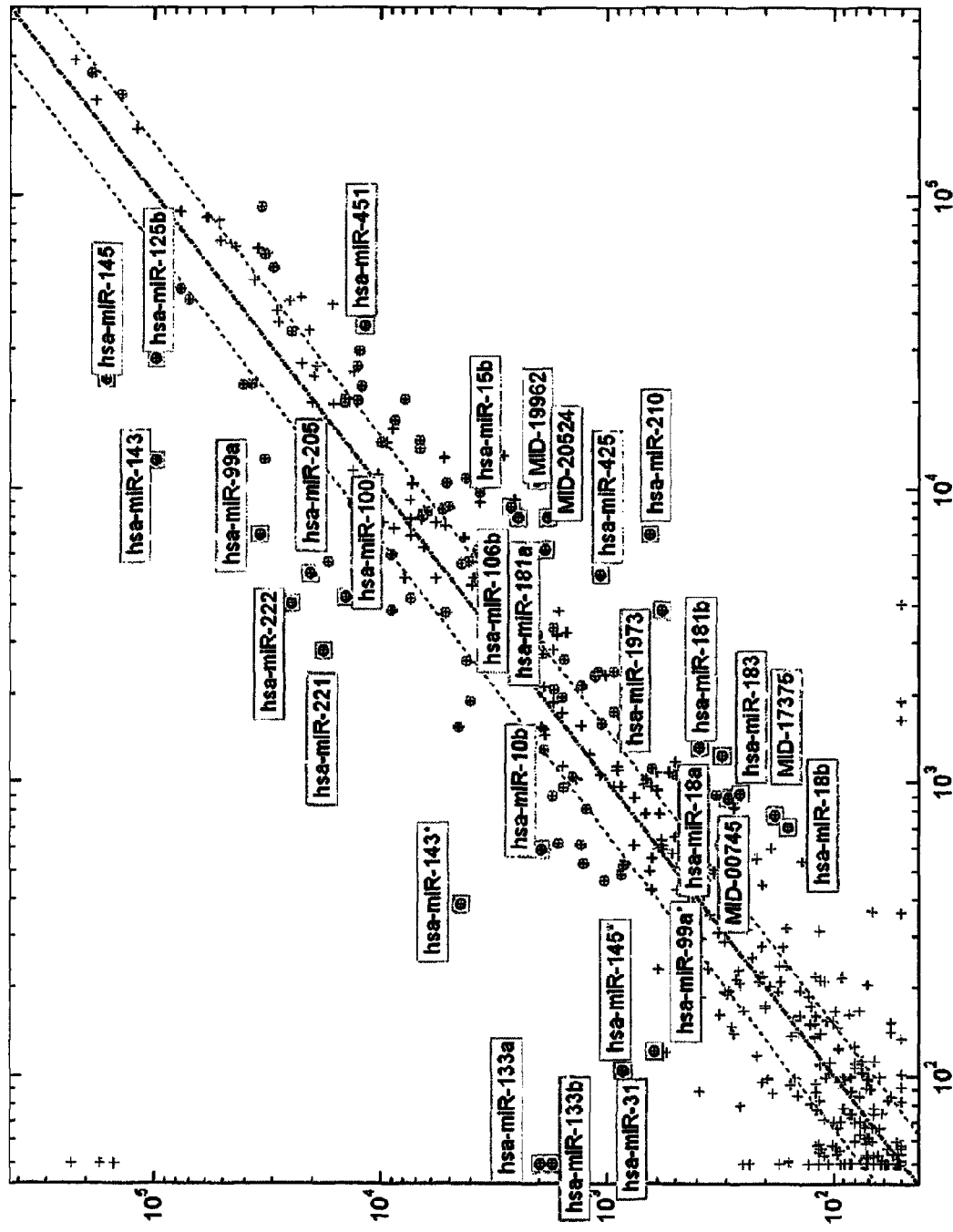
FIG. 1 shows differential expression of miRs (in $\log_2$(fluorescence units)), comparing the median values of each miR in primary tumors obtained from prostate cancer patients (n=18) (y-axis) with the corresponding median for prostate metastases (n=9) x-axis). The parallel lines describe a fold change between groups of 1.5 in either direction. Statistically significant miRs (P-value<0.05) are marked with circles: hsa-miR-145 (SEQ ID NO: 6), hsa-miR-143 (SEQ ID NO: 7), hsa-miR-125b (SEQ ID NO: 14), hsa-miR-99a (SEQ ID NO: 15), hsa-miR-222 (SEQ ID NO: 17), hsa-miR-221 (SEQ ID NO: 21), hsa-miR-205 (SEQ ID NO: 1), hsa-miR-451 (SEQ ID NO: 87), hsa-miR-143* (SEQ ID NO: 4), hsa-miR-100 (SEQ ID NO: 16), hsa-miR-15b (SEQ ID NO: 28), hsa-miR-133a (SEQ ID NO: 2), hsa-miR-133b (SEQ ID NO: 3), hsa-miR-10b (SEQ ID NO: 8), hsa-miR-31 (SEQ ID NO: 71), hsa-miR-145* (SEQ ID NO: 5), hsa-miR-99a* (SEQ ID NO: 73), hsa-miR-425 (SEQ ID NO: 29), hsa-miR-106b (SEQ ID NO: 35), hsa-miR-181a (SEQ ID NO: 30), hsa-miR-181b (SEQ ID NO: 27), hsa-miR-18a (SEQ ID NO: 85), hsa-miR-1973 (SEQ ID NO: 75), hsa-miR-18b (SEQ ID NO: 79), hsa-miR-183 (SEQ ID NO: 31) and hsa-miR-210 (SEQ ID NO: 26).
Figure 3A:
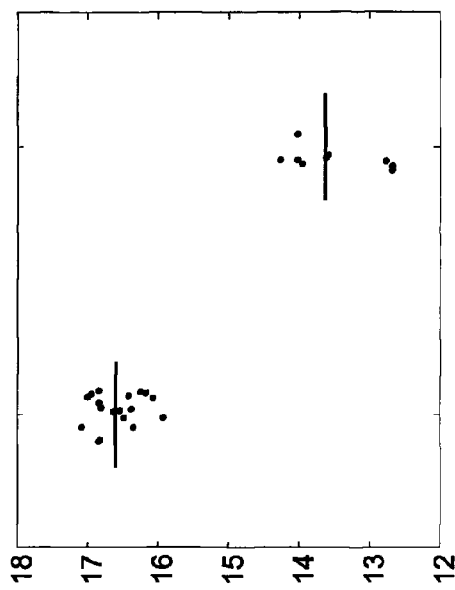
FIGS. 3A-D are dot plot presentations comparing the group of patients with primary prostate cancer (the left box) with the group of patients with metastatic prostate cancer (the right box), with regard to expression (in $\log_2$(fluorescence units)) of the following miRs.
Figure 3B:
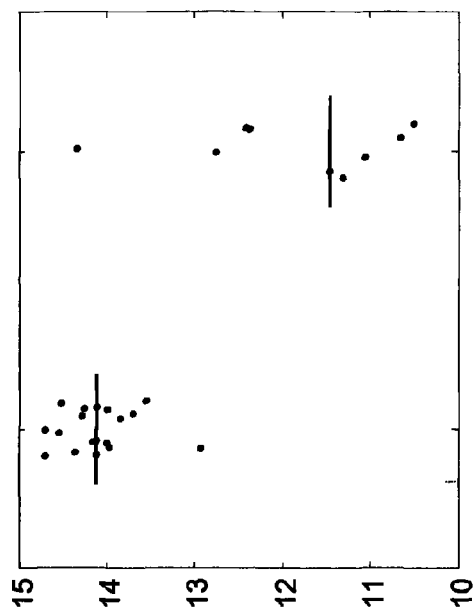
Figure 3C:
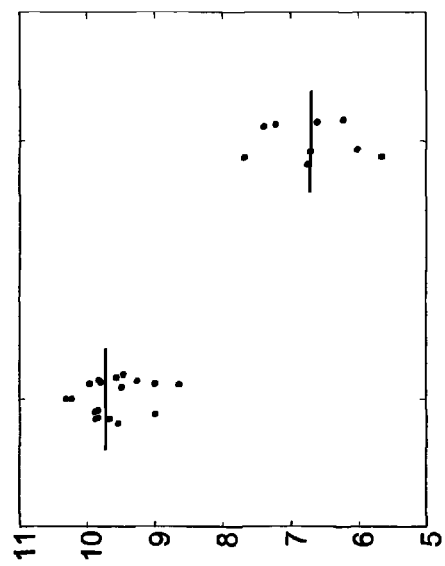
Figure 3D:
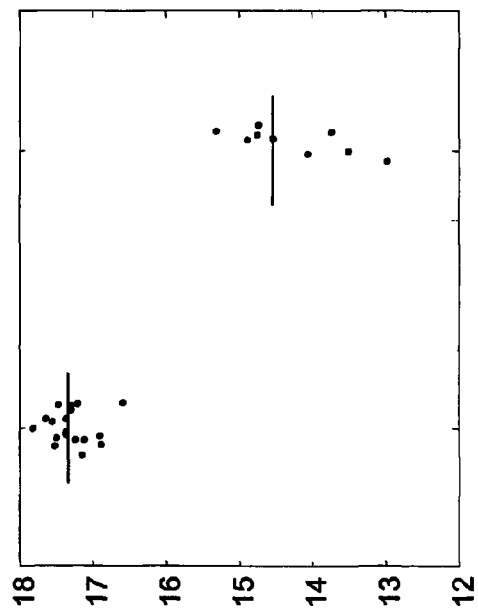
Figure 5B:
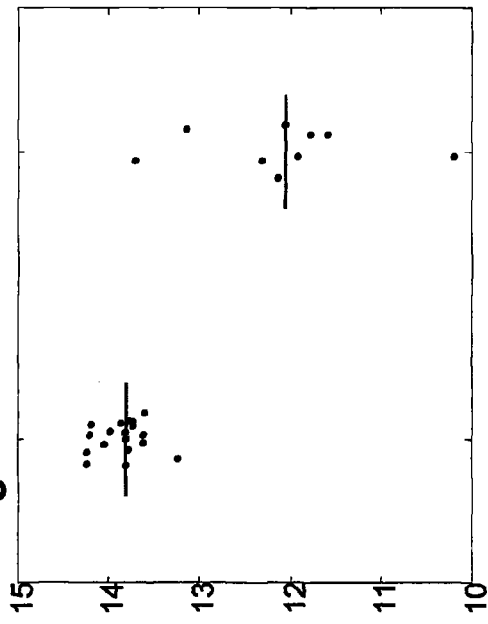
FIGS. 5A-D are dot plot presentations comparing the group of patients with primary prostate cancer (the left box) with the group of patients with metastatic prostate cancer (the right box), with regard to expression (in $\log_2$(fluorescence units)) of the following miRs.
Figure 5D:
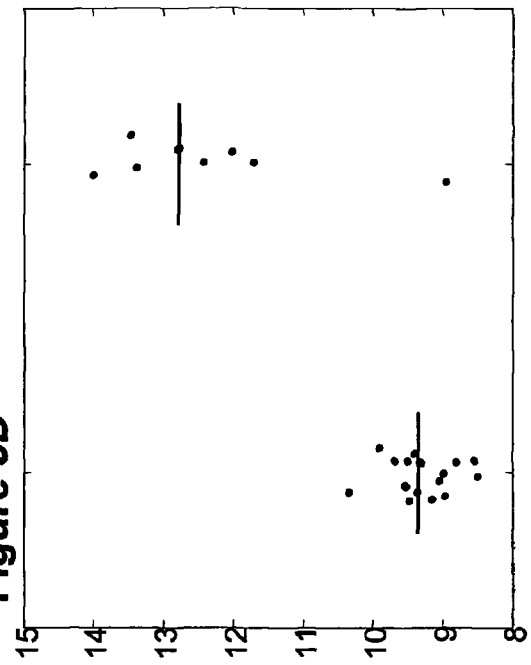
Figure 5A:
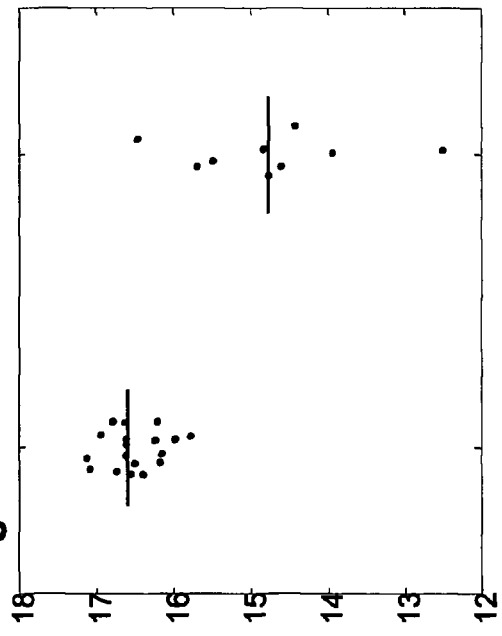
Figure 5C:
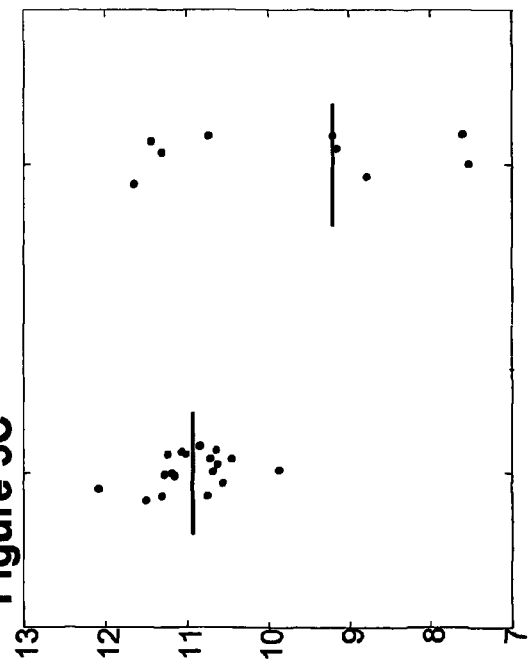
Figure 7A:
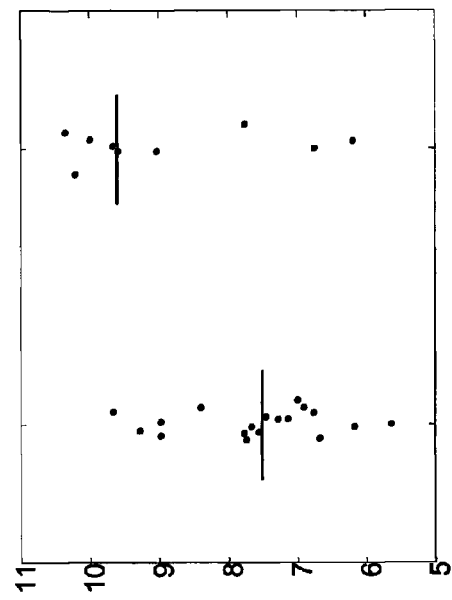
FIGS. 7A-D are dot plot presentations comparing the group of patients with primary prostate cancer (the left box) with the group of patients with metastatic prostate cancer (the right box), with regard to expression (in $\log_2$(fluorescence units)) of the following miRs.
Figure 7B:
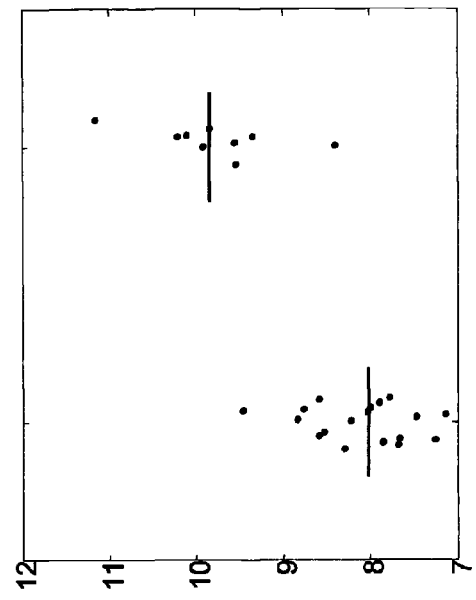
Figure 7C:
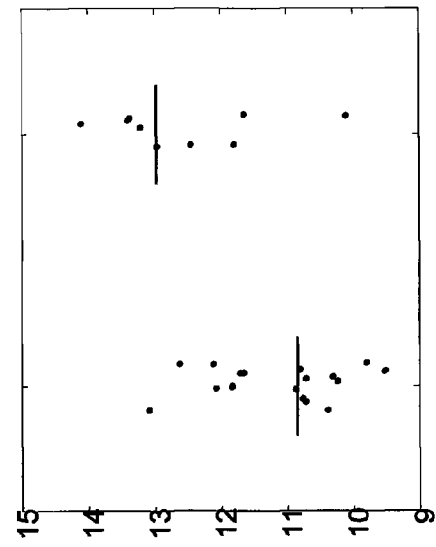
Figure 7D:
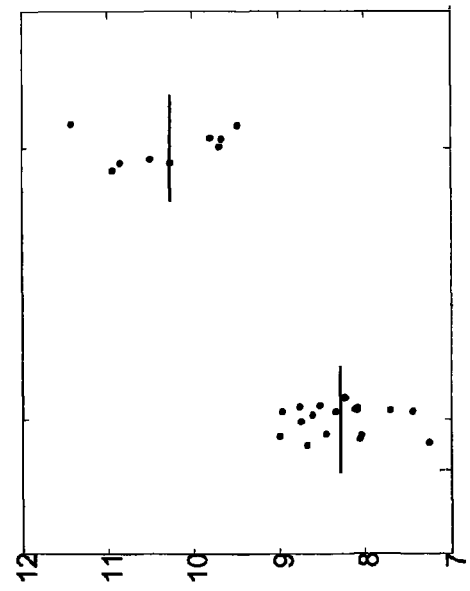
Figure 8B:
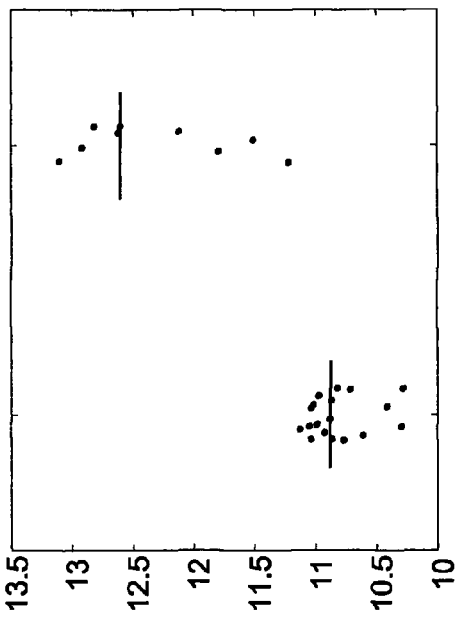
FIGS. 8A-D are dot plot presentations comparing the group of patients with primary prostate cancer (the left box) with the group of patients with metastatic prostate cancer (the right box), with regard to expression (in $\log_2$(fluorescence units)) of the following miRs.
Figure 8D:
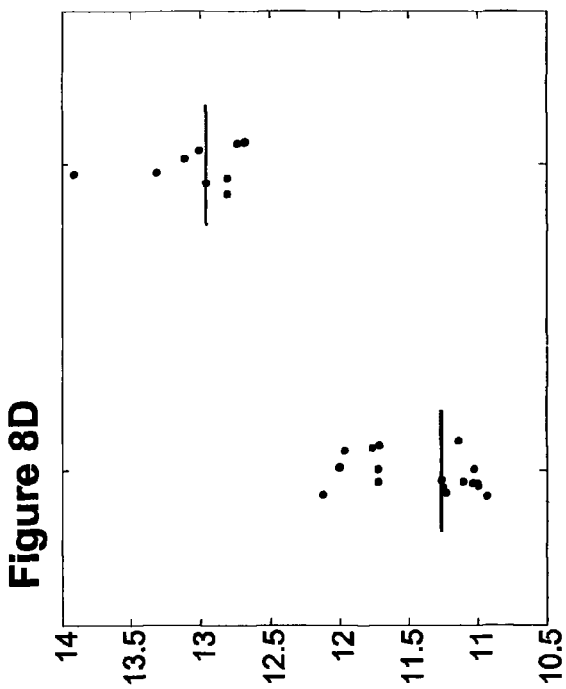
Figure 8A:
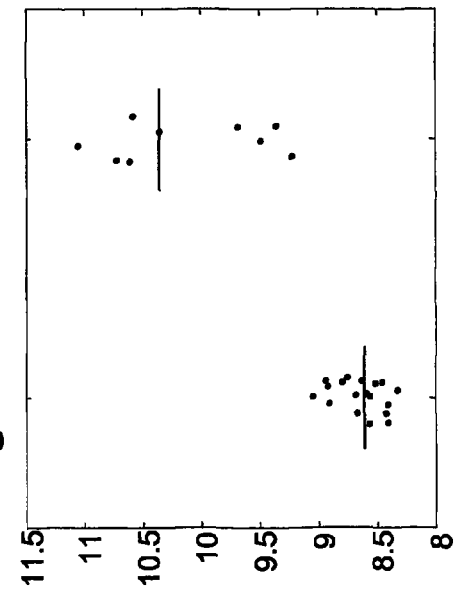
Figure 8C:
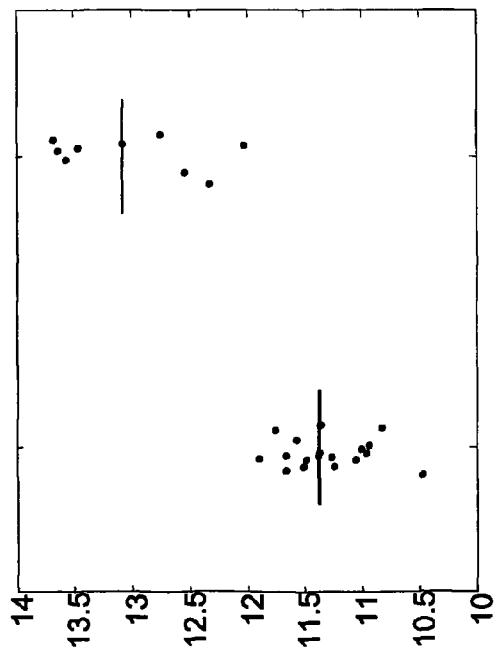
Figure 9:
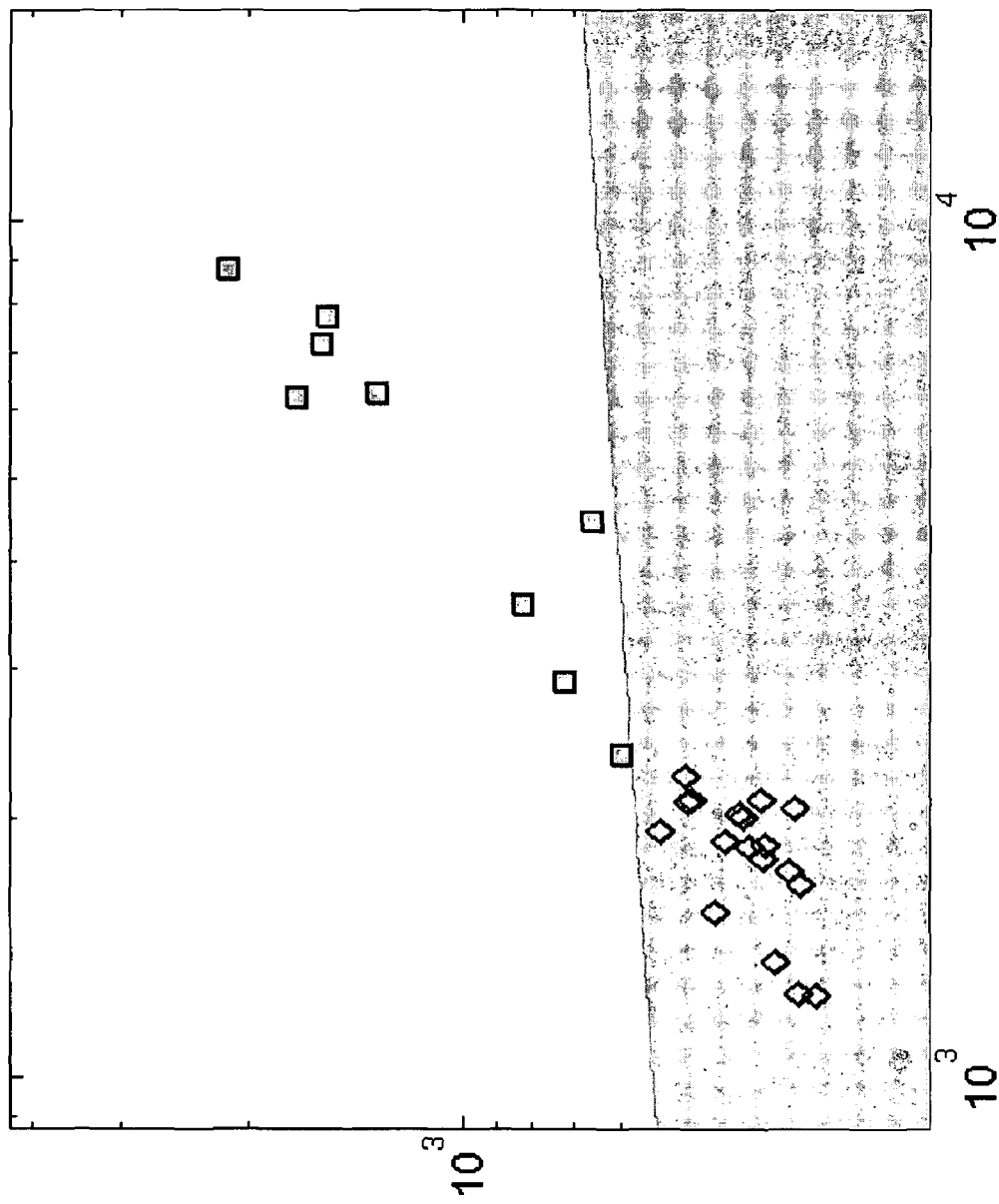
FIG. 9 demonstrates the classification of prostate primary tumors (diamond symbols) and prostate metastases (square symbols) using the expression levels of two microRNA biomarkers: hsa-miR-181b (SEQ ID NO: 27, Y-axis) and hsa-miR-181a (SEQ ID NO: 30, X-axis) that have different expression levels in these groups.
Figure 10:
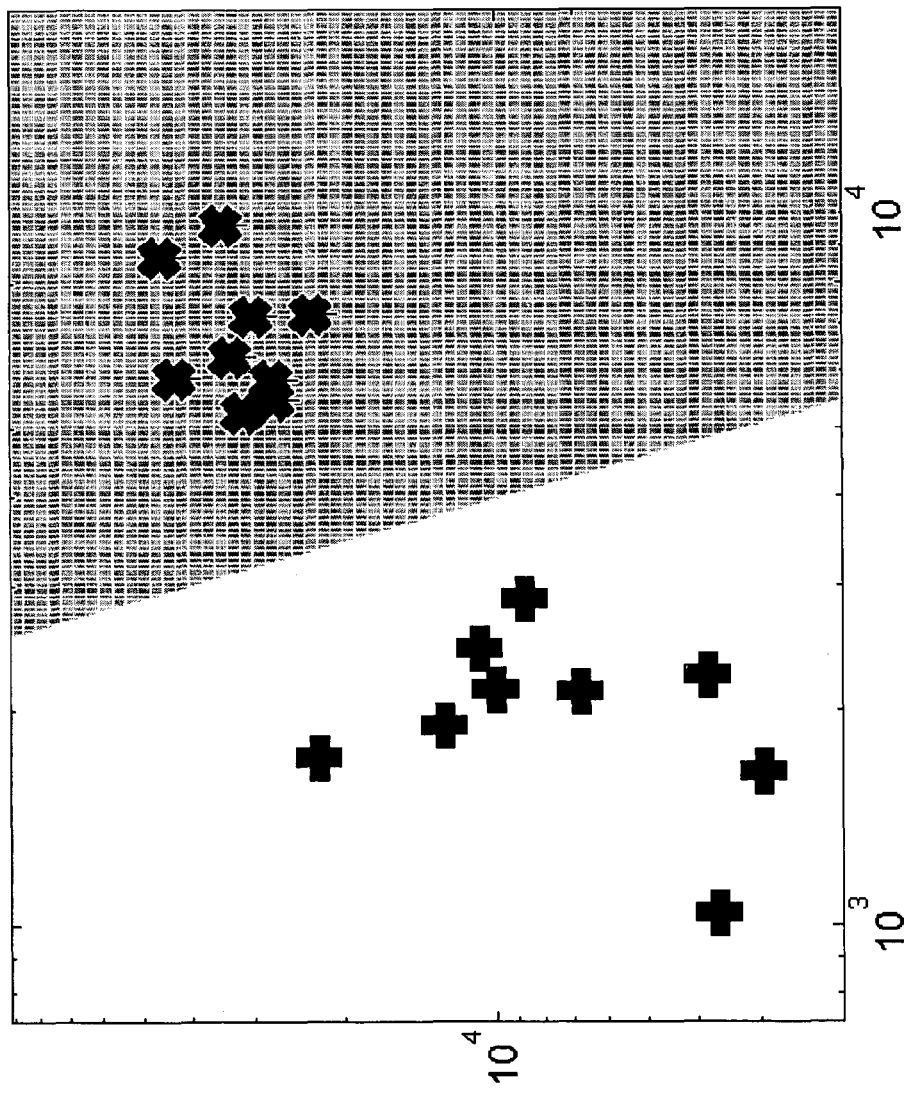
FIG. 10 demonstrates the classification of prostate primary tumors (X symbols) and prostate metastases (cross symbols) using the expression levels of two microRNA biomarkers: hsa-miR-99a (SEQ ID NO: 15, Y-axis) and hsa-miR-100 (SEQ ID NO: 16, X-axis).

High Expression of Selective miRs is Characteristic of Patients with Primary Prostate Cancer As indicated in FIG. 1, the expression of each of hsa-miR-145 (SEQ ID NO: 6), hsa-miR-143 (SEQ ID NO: 7), hsa-miR-125b (SEQ ID NO: 14), hsa-miR-205 (SEQ ID NO: 1), hsa-miR-100 (SEQ ID NO: 16), hsa-miR-99a (SEQ ID NO: 15), hsa-miR-222 (SEQ ID NO: 17), hsa-miR-221 (SEQ ID NO: 21), hsa-miR-143* (SEQ ID NO: 4), hsa-miR-133b (SEQ ID NO: 3), hsa-miR-31 (SEQ ID NO: 71), hsa-miR-145* (SEQ ID NO: 5), hsa-miR-10b (SEQ ID NO: 8), hsa-miR-99a* (SEQ ID NO: 73) and hsa-miR-133a (SEQ ID NO: 2), is higher in patients with primary prostate cancer as compared to patients with prostate metastases. In contrast, the expression of each of hsa-miR-210 (SEQ ID NO: 26), hsa-miR-451 (SEQ ID NO: 87), hsa-miR-15b (SEQ ID NO: 28), hsa-miR-425 (SEQ ID NO: 29), hsa-miR-106b (SEQ ID NO: 35), hsa-miR-181a (SEQ ID NO: 30), hsa-miR-181b (SEQ ID NO: 27), hsa-miR-18a (SEQ ID NO: 85), hsa-miR-1973 (SEQ ID NO: 75), hsa-miR-18b (SEQ ID NO: 79) and hsa-miR-183 (SEQ ID NO: 31) is higher in patients with prostate metastases as compared to patients with primary prostate cancer.

The fold change between the expression of the miRs in patients with primary prostate cancer and prostate metastases, and the corresponding p-values, are listed in Table 1 (first experiment) and Table 2 (second experiment) below.

TABLE 1A

Up regulated in prostate primary tumors vs. prostate metastases:

| miR name | miR SEQ ID NO: | hairpin SEQ ID NO: | p-value | fold change | median values | |
|---|---|---|---|---|---|---|
| hsa-miR-205 | 1 | 37 | 2.0e−004 | 247.18(+) | 1.2e+004 | 5.0e+001 |
| hsa-miR-133a | 2 | 38 | 2.4e−016 | 24.94(+) | 1.2e+003 | 5.0e+001 |
| hsa-miR-133b | 3 | 39 | 2.8e−015 | 23.23(+) | 1.2e+003 | 5.0e+001 |
| hsa-miR-143* | 4 | 40 | 2.3e−013 | 21.49(+) | 1.1e+003 | 5.0e+001 |
| hsa-miR-145* | 5 | 41 | 6.2e−014 | 12.27(+) | 6.1e+002 | 5.0e+001 |
| hsa-miR-145 | 6 | 41 | 2.3e−008 | 11.35(+) | 1.0e+005 | 9.1e+003 |
| hsa-miR-143 | 7 | 40 | 9.3e−010 | 10.93(+) | 6.0e+004 | 5.5e+003 |
| hsa-miR-10b | 8 | 42 | 8.1e−004 | 8.84(+) | 2.1e+003 | 2.3e+002 |
| hsa-miR-214* | 9 | 43 | 2.7e−006 | 5.85(+) | 1.5e+003 | 2.5e+002 |
| hsa-miR-199a-5p | 10 | 44 | 7.2e−004 | 5.23(+) | 1.2e+004 | 2.3e+003 |
| hsa-miR-199b-5p | 11 | 45 | 1.9e−004 | 5.22(+) | 2.8e+003 | 5.4e+002 |
| hsa-miR-214 | 12 | 43 | 2.0e−003 | 4.10(+) | 2.7e+003 | 6.7e+002 |
| hsa-miR-199a-3p | 13 | 44 | 2.9e−004 | 4.03(+) | 1.2e+004 | 2.9e+003 |
| hsa-miR-125b | 14 | 47 | 1.3e−005 | 3.67(+) | 6.1e+004 | 1.7e+004 |
| hsa-miR-99a | 15 | 48 | 1.2e−005 | 3.61(+) | 3.2e+004 | 8.8e+003 |
| hsa-miR-100 | 16 | 49 | 1.8e−008 | 2.95(+) | 6.3e+003 | 2.1e+003 |
| hsa-miR-222 | 17 | 50 | 1.5e−002 | 2.90(+) | 1.4e+004 | 4.8e+003 |
| hsa-miR-130a | 18 | 51 | 1.4e−003 | 2.83(+) | 3.9e+003 | 1.4e+003 |
| hsa-miR-125a-5p | 19 | 52 | 4.2e−003 | 2.53(+) | 4.8e+003 | 1.9e+003 |
| hsa-miR-455-3P | 20 | 53 | 1.6e−002 | 2.50(+) | 7.1e+002 | 2.8e+002 |
| hsa-miR-221 | 21 | 54 | 3.9e−002 | 2.36(+) | 9.9e+003 | 4.2e+003 |
| hsa-miR-152 | 22 | 55 | 4.6e−003 | 2.06(+) | 1.1e+003 | 5.3e+002 |
| hsa-miR-30a | 23 | 56 | 1.8e−002 | 2.04(+) | 3.1e+003 | 1.5e+003 |
| hsa-miR-26b | 24 | 57 | 3.7e−003 | 2.04(+) | 2.9e+003 | 1.4e+003 |
| hsa-miR-29c* | 25 | 58 | 6.4e−003 | 2.01(+) | 1.0e+003 | 5.0e+002 |

TABLE 1B

Down regulated in prostate primary tumors vs. prostate metastases:

| miR name | miR SEQ ID NO: | hairpin SEQ ID NO: | p-value | fold change | median values | |
|---|---|---|---|---|---|---|
| hsa-miR-210 | 26 | 59 | 1.3e−005 | 15.81(−) | 3.0e+002 | 4.8e+003 |
| hsa-miR-181b | 27 | 60, 61 | 4.2e−004 | 4.79(−) | 3.6e+002 | 1.7e+003 |
| hsa-miR-15b | 28 | 62 | 1.1e−006 | 4.19(−) | 2.5e+003 | 1.0e+004 |
| hsa-miR-425 | 29 | 63 | 2.7e−007 | 4.16(−) | 6.7e+002 | 2.8e+003 |
| hsa-miR-181a | 30 | 64 | 7.6e−005 | 3.75(−) | 1.6e+003 | 5.9e+003 |
| hsa-miR-183 | 31 | 65 | 1.8e−003 | 3.07(−) | 2.5e+002 | 7.7e+002 |
| hsa-miR-130b | 32 | 66 | 2.0e−004 | 2.81(−) | 2.7e+002 | 7.6e+002 |
| hsa-miR-223 | 33 | 67 | 4.3E−002 | 2.58(−) | 8.4e+002 | 2.2e+003 |
| hsa-miR-182 | 34 | 68 | 8.4e−005 | 2.48(−) | 9.4e+002 | 2.3e+003 |
| hsa-miR-106b | 35 | 69 | 1.2e−005 | 2.47(−) | 2.4e+003 | 6.0e+003 |
| hsa-miR-21 | 36 | 70 | 3.7e−003 | 2.28(−) | 2.2e+004 | 5.1e+004 |

TABLE 2A

Up regulated in prostate primary tumors vs. prostate metastases:

| miR name | miR SEQ ID NO. | hairpin SEQ ID NO. | p-value | fold-change | median values | |
|---|---|---|---|---|---|---|
| hsa-miR-133a | 2 | 38 | 1.90E−19 | 39.51 (+) | 2.00E+03 | 5.00E+01 |
| hsa-miR-133b | 3 | 39 | 5.90E−18 | 34.82 (+) | 1.70E+03 | 5.00E+01 |
| hsa-miR-143* | 4 | 40 | 1.70E−12 | 11.43 (+) | 4.40E+03 | 3.90E+02 |
| hsa-miR-31 | 71 | 72 | 2.30E−05 | 8.25 (+) | 8.60E+02 | 1.00E+02 |
| hsa-miR-145* | 5 | 41 | 3.40E−13 | 8.09 (+) | 8.40E+02 | 1.00E+02 |
| hsa-miR-143 | 7 | 40 | 7.90E−15 | 7.82 (+) | 9.80E+04 | 1.30E+04 |
| hsa-miR-145 | 4 | 41 | 4.90E−14 | 6.87 (+) | 1.60E+05 | 2.40E+04 |
| hsa-miR-221 | 21 | 54 | 2.30E−07 | 6.32 (+) | 1.80E+04 | 2.80E+03 |
| hsa-miR-222 | 17 | 50 | 3.20E−08 | 6.03 (+) | 2.50E+04 | 4.10E+03 |
| hsa-miR-99a* | 73 | 74 | 4.70E−05 | 5.09 (+) | 6.20E+02 | 1.20E+02 |
| hsa-miR-99a | 15 | 48 | 2.20E−05 | 4.87 (+) | 3.40E+04 | 7.00E+03 |
| hsa-miR-205 | 1 | 37 | 3.30E−03 | 3.98 (+) | 2.00E+04 | 5.10E+03 |
| hsa-miR-125b | 14 | 47 | 2.40E−06 | 3.53 (+) | 9.80E+04 | 2.80E+04 |
| hsa-miR-100 | 16 | 49 | 1.50E−07 | 3.36 (+) | 1.40E+04 | 4.30E+03 |
| hsa-miR-10b | 8 | 42 | 5.60E−03 | 3.28 (+) | 1.90E+03 | 5.90E+02 |

TABLE 2B

Down regulated in prostate primary tumors vs. prostate metastases:

| miR name | miR SEQ ID NO: | hairpin SEQ ID NO: | p-value | fold-change | median values | |
|---|---|---|---|---|---|---|
| hsa-miR-210 | 26 | 59 | 1.30E−08 | 10.88 (−) | 6.50E+02 | 7.00E+03 |
| hsa-miR-1973 | 75 | 76 | 4.60E−03 | 6.78 (−) | 5.70E+02 | 3.90E+03 |
| MID-19962 | 77 | 78, 91 | 1.70E−02 | 5.25 (−) | 2.00E+03 | 1.10E+04 |
| hsa-miR-425 | 29 | 63 | 5.90E−13 | 4.79 (−) | 1.10E+03 | 5.10E+03 |
| hsa-miR-18b | 79 | 80 | 3.20E−07 | 4.44 (−) | 1.60E+02 | 7.00E+02 |
| MID-20524 | 81 | 82 | 3.80E−03 | 4.39 (−) | 1.80E+03 | 8.00E+03 |
| MID-17375 | 83 | 84 | 2.50E−02 | 4.28 (−) | 1.80E+02 | 7.70E+02 |
| hsa-miR-18a | 85 | 86 | 3.90E−09 | 3.96 (−) | 3.10E+02 | 1.20E+03 |
| hsa-miR-183 | 31 | 65 | 1.40E−06 | 3.54 (−) | 2.60E+02 | 9.10E+02 |
| hsa-miR-181b | 27 | 60, 61 | 7.00E−09 | 3.37 (−) | 3.90E+02 | 1.30E+03 |
| hsa-miR-181a | 30 | 64 | 9.80E−09 | 3.31 (−) | 1.90E+03 | 6.20E+03 |
| hsa-miR-15b | 28 | 62 | 2.80E−09 | 3.27 (−) | 2.60E+03 | 8.70E+03 |
| hsa-miR-106b | 35 | 69 | 8.20E−10 | 3.26 (−) | 2.40E+03 | 8.00E+03 |
| hsa-miR-451 | 87 | 88 | 3.80E−03 | 3.07 (−) | 1.20E+04 | 3.60E+04 |
| MID-00745 | 89 | 90 | 2.80E−02 | 3.02 (−) | 2.90E+02 | 8.80E+02 |

Example 3

Proliferation Assay Using Anti-miRs in Prostate Cancer Cell Lines

The proliferation inhibition of prostate cancer cell lines after treatment with anti-miRs sequences (Table 3) is shown in FIGS. 12A-B. Anti-miRs 21, 210 and 191 gave best proliferation inhibition response in both cell lines. Anti-miRs 181a, 181b and 106b gave moderate proliferation inhibition response. All results were compared to the inactive control of anti-miR molecule with similar chemical modifications and an irrelevant sequence.

TABLE 3

Anti-miRs sequences

| Antisense sequence | SEQ ID NO: | Target name |
|---|---|---|
| CACAAGUUCGGAUCUACGGGUU | 92 | hsa-miR-100 |
| AUCUGCACUGUCAGCACUUUA | 93 | hsa-miR-106b |
| ACUCACCGACAGCGUUGAAUGUU | 94 | hsa-miR-181a |
| ACCCACCGACAGCAAUGAAUGUU | 95 | hsa-miR-181b |
| CAGCUGCUUUUGGGAUUCCGUUG | 96 | hsa-miR-191 |
| UCAACAUCAGUCUGAUAAGCUA | 97 | hsa-miR-21 |
| UCAGCCGCUGUCACACGCACAG | 98 | hsa-miR-210 |
| CACAAAUUCGGUUCUACAGGGUA | 99 | hsa-miR-10b |
| ACAUACUCCUUUCUCAGAGUCCA | 100 | negative control |

Example 4

Anti-miR and miR-Mimic for Therapeutics of Prostate Cancer Metastasis

PC-3 and DU 145, both human prostate carcinoma cell lines established from a bone and brain metastasis respectively, are used to prepare orthotopic prostate xenografts in nod scid mice (Bastide et al., 2002, Prostate Cancer and Prostatic Diseases 5, 311-315).

In short, 8 to 10-week-old male mice are anesthetized and implanted with prostate cells. Implantation is made under surgical sterile conditions. The abdomen is cleaned with iodine solution and a 1 cm midline incision is made to expose the prostate gland. One million cells suspended in 50 ul of PBS are injected into a dorsal prostatic lobe. The abdominal wound is closed surgically.

Treatment of anti-miRs 21, 191 and 210 is conducted by IV or IP injection to the mice, 2 days after implantation of orthotopic tumor, and is given repeatedly for up to weeks. At the end of the study (week 11-12) an autopsy is performed to assess the distribution of metastases. Prostatic tumors and metastases are harvested, weighed and divided to two; one half is fixed in 10% formalin for histological analysis and another half is for RNA extraction for miR quantification (qRT-PCR). The efficacy is evaluated by assessing the metastatic tumor burden.

A similar methodology is used with miR-mimetic of microRNAs that are down regulated in prostate metastases.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

---

The invention claimed is:

1. A method for distinguishing between primary prostate cancer and prostate metastases in a subject with prostate cancer and determining a prognosis and a therapeutic strategy for the subject with prostate cancer based on the distinction between primary prostate cancer and prostate metastases, comprising:
(a) providing a biological sample from the subject;
(b) determining the expression level of SEQ ID NO: 1 in said sample;
(c) comparing said expression level to a threshold expression level,
wherein an altered expression level of SEQ ID NO: 1 compared to said threshold expression level allows the distinction between primary prostate cancer and prostate metastases; and
(d) determining the prognosis and therapeutic strategy for said subject based on the distinction between primary prostate cancer and prostate metastases.

2. The method of claim 1, wherein an increased expression level of SEQ ID NO: 1 compared to said threshold expression level is indicative of good prognosis of said subject.

3. The method of claim 1, wherein the subject is a human.

4. The method of claim 1, wherein said method is used to determine a course of treatment for said subject.

5. The method of claim 1, wherein said biological sample is selected from the group consisting of bodily fluid, a cell line and a tissue sample.

6. The method of claim 5, wherein said bodily fluid is blood.

7. The method of claim 5, wherein said tissue is a fresh, frozen, fixed, wax-embedded or formalin fixed paraffin-embedded (FFPE) tissue.

8. The method of claim 7, wherein said tissue is a prostate cancer tissue.

9. The method of claim 1, wherein the expression level is determined by a method selected from the group consisting of nucleic acid hybridization, nucleic acid amplification, and a combination thereof.

10. The method of claim 9, wherein the nucleic acid hybridization is performed using a solid-phase nucleic acid biochip array or in situ hybridization.

11. The method of claim 9, wherein the nucleic acid amplification method is real-time PCR.

12. The method of claim 11, wherein the real-time PCR method comprises forward and reverse primers.

13. The method of claim 12, wherein the real-time PCR method further comprises a probe.

14. The method of claim 13, wherein the probe comprises a sequence complementary to SEQ ID NO: 1.

15. A kit for determining a prognosis of a subject with prostate cancer, said kit comprising a forward primer comprising a nucleic acid sequence that is complementary to a sequence selected from SEQ ID NO: 1.

16. The kit of claim 15, wherein the kit further comprises a probe.

17. The kit of claim 16, wherein the probe comprising a nucleic acid sequence that is complementary to a sequence selected from SEQ ID NO: 1.

* * * * *